United States Patent [19]

Curtiss, III

[11] Patent Number: 4,968,619

[45] Date of Patent: Nov. 6, 1990

[54] MODIFIED MICROORGANISMS AND METHOD OF PREPARING AND USING SAME

[75] Inventor: Roy Curtiss, III, St. Louis, Mo.

[73] Assignee: Research Corporation, New York, N.Y.

[21] Appl. No.: 513,237

[22] Filed: Oct. 17, 1983

Related U.S. Application Data

[60] Continuation of Ser. No. 90,640, Nov. 2, 1979, abandoned, which is a division of Ser. No. 727,365, Sep. 27, 1976, Pat. No. 4,190,495.

[51] Int. Cl.$^5$ .................... C12R 1/185; C12N 15/00
[52] U.S. Cl. ..................... 435/252.33; 435/172.3; 435/252.8; 435/849
[58] Field of Search .................. 435/172.3, 253, 849, 435/252.33, 252.8

[56] References Cited

U.S. PATENT DOCUMENTS

4,237,224  12/1980  Cohen et al. ..................... 435/172.3

OTHER PUBLICATIONS

Pelczar et al, Microbiology, McGraw-Hill Book Company, New York, pp. 485–487 (1972).
J. Mol. Biol., vol. 53, pp. 159–162 (1970).
Miller, Experiments in Molecular Genetics, Cold Spring Harbor Laboratory, New York, 1972.
Adler et al, Proc. Nat. Acad. Sci., vol. 57, pp. 321–326 (1967).
Bachmann, Bacteriol Rev., vol. 40, pp. 525–557, 1972.
Fraser et al, Curr. Topics Microbiol. Immunol., vol. 69, pp. 1–84 (1975).

*Primary Examiner*—Charles F. Warren
*Assistant Examiner*—David T. Fox
*Attorney, Agent, or Firm*—Scully, Scott, Murphy & Presser

[57] ABSTRACT

Microorganisms have been developed which may be characterized as possessing substantially all of the following qualities or capabilities:

(a) capable of having foreign genetic information introduced thereinto and recovered therefrom along with its expression with production of useful gene products;

(b) the microorganism being dependent for growth and survival upon defined conditions;

(c) the microorganism being incapable of establishment or growth or colonization and/or survival under conditions or in ecological niches that are considered to be natural and/or undesirable for said microorganism;

(d) the microorganism being capable of causing genetic information incorporated therein to undergo degradation under conditions or ecological niches that are considered to be natural and/or undesirable for said microorganism;

(e) the microorganism being capable of permitting cloning vectors incorporated therein to be dependent for their replication, maintenance and/or function on said microorganism;

(f) the microorganism being substantially incapable of transmitting cloning vectors or recombinant DNA molecules incorporated therein to other organisms under conditions or ecological niches that are considered to be natural and/or undesirable for said microorganism;

(g) the microorganism being capable of being monitored by suitable means and/or techniques without substantial alteration of said microorganism; and (h) the microorganism being susceptible of substantially minimal contamination with other organisms when recombinant DNA molecules are incorporated therein and being substantially incapable of contaminating other organisms when incorporated therein or consumed thereby when recombinant DNA molecules are incorporated in said microorganism.

20 Claims, No Drawings

MODIFIED MICROORGANISMS AND METHOD OF PREPARING AND USING SAME

The Government has rights in this invention pursuant to Grant GB-37546 awarded by the National Science Foundation. The invention described herein was made in the course of work under the above grant from the National Science Foundation and Grant Number NIAI-DAI-11456 and NIDR DE-02670 from the Department of Health, Education and Welfare.

This application is a continuation of application Ser. No. 06/090,640, filed Nov. 2, 1979, now Abandoned, which is a Division of application Ser. No. 05/727,365, filed Sept. 27, 1976, now U.S. Pat. No. 4,190,495.

This invention relates to the development of microorganisms possessing special properties. More particularly, this invention is concerned with the genetic alteration of microorganisms, such as *Escherichia coli*, to impart special properties thereto, particularly genetically-linked properties. It is known to effect genetic changes in microorganisms by exposing microorganisms to radiation, such as ultraviolet radiation, x-ray radiation or by exposure to chemical mutagens. Many genetically-altered microorganisms produced by such techniques are of substantial value and utility, not only in commerce and medicine but also in research.

One area of research of special interest, not only because it might make available special microorganisms heretofore unknown which are useful in medicine for the treatment of diseases, but also because such heretofore unknown microorganisms might present unique biohazards, involves recombinant DNA molecules. Techniques are known and have been developed for inserting recombinant DNA molecule, e.g. plasmid or viral cloning vector DNA containing DNA molecules from any organism or virus, into microorganisms into which they have been inserted. The potential utility and hazards of such recombinant DNA molecular research have received wide publication.

It is an object of this invention to provide a vehicle or structure or cellular material or microorganism useful in recombinant DNA research activities.

It is another object of this invention to provide techniques for altering the properties, particularly the genetic properties or structure, of cellular material, such as bacteria, yeast and the like.

How these and other objects are achieved will become apparent in the light of the accompanying disclosure. In at least one embodiment of the practice of this invention at least one of the foregoing objects will be achieved.

Microorganisms have been developed which may be characterized as possessing substantially all of the following qualities or capabilities:

(a) capable of having foreign genetic information introduced thereinto and recovered therefrom along with its expression with production of useful gene products;

(b) the microorganism being dependent for growth and survival upon defined conditions;

(c) the microorganism being incapable of establishment or growth or colonization and/or survival under conditions or in ecological niches that are considered to be natural and/or undesirable for said microorganism;

(d) the microorganism being capable of causing genetic information incorporated therein to undergo degradation under conditions or ecological niches that are considered to be natural and/or undesirable for said microorganism;

(e) the microorganism being capable of permitting cloning vectors incorporated therein to be dependent for their replication, maintenance and/or function on said microorganism;

(f) the microorganism being substantially incapable of transmitting cloning vectors or recombinant DNA molecules incorporated therein to other organisms under conditions or ecological niches that are considered to be natural and/or undesirable for said microorganism;

(g) the microorganism being capable of being monitored by suitable means and/or techniques without substantial alteration of said microorganism; and (h) the microorganism being susceptible of substantially minimal contamination with other organisms when recombinant DNA molecules are incorporated therein and being substantially incapable of contaminating other organisms when incorporated therein or consumed thereby when recombinant DNA molecules are incorporated in said microorganism.

In developing or producing microorganisms as described hereinabove, deletion mutations and/or two mutations affecting the same function are desirably employed whenever possible to preclude or greatly diminish the probability or possibility that the strain can lose the property conferred by such mutation or mutations. Examples of such microorganisms are *Escherichia coli* K-12 $\chi$1776, *Escherichia coli* K-12 $\chi$1972, *Escherichia coli* K-12 $\chi$1976 and *Escherichia coli* K-12 $\chi$2076. Additionally, techniques have been developed and employed for imparting special properties, e.g. genetic properties, to microorganisms which render the resulting microorganism unique.

Also, techniques have been developed for the handling of plasmid cloning DNA vectors for eventual insertion into microorganisms for testing therein, such as the above-mentioned microorganisms, and techniques have been developed for the transformation of microorganisms, such as the above-identified microorganisms, for the introduction of recombinant DNA molecules thereinto. Also techniques have been developed in connection with the development or production of the above-identified microorganisms which impart special genetically-linked properties thereto, which techniques are applicable to a large number and diversity of microorganisms, including not only bacteria but also yeast and other cellular material.

Although emphasis has been placed in the disclosure of this invention with respect to the usefulness of the special microorganisms of this invention in recombinant DNA research, special microorganisms prepared in accordance with the teachings of this invention would have wide ranging utility. For example, microorganisms, such as yeast cells, could be prepared having special properties which permit ready lysing or breakdown of the yeast cells, e.g. yeast cells having a substantially weakened wall structure. Bacterial microorganisms having weakened wall structures and/or other special physical properties are also capable of being prepared in accordance with this invention. Additionally, as indicated hereinabove with respect to *E. coli*, not only are the *E. coli* microorganisms of this invention useful in recombinant DNA research activities but also *E. coli* microorganisms which may be produced in accordance with the practice of this invention would be useful in sewage treatment plants or fermentation plants, such as fermentation plants based on *E. coli* for the fermentation of glucose to produce a mixture of commercially valuable organic acids. It is known that *E. coli* fermentation of glucose results in a mixture of organic acids, e.g. succinic acid, lactic acid, acetic acid and formic acid as well as other commercially useful products.

In the practices of this invention, particularly for the development of microorganisms having the properties indicated hereinabove, such as the production of the microorganism *E. coli* K-12 $\chi$1776, and for the production of other microorganisms, such as $\chi$1972, $\chi$1976 and $\chi$2076, also substantially possessing the desirable properties set forth hereinabove, for the production of other microorganisms, e.g. genetically altered microorganisms, certain techniques for the induction, isolation and characterization of mutations have been developed. For example, Mutation Chart A enumerates and describes properties of mutations alone or in combination that have been shown to confer the desirable properties set forth hereinabove.

MUTATION CHART A

The gene symbol designations are those used by Bachmann, et al. (Bacteriol. Rev. 40:116-167, 1976) for known genes and for unknown genes identified during development of this invention, follow the conventions of genetic nomenclature proposed by Demerec, et al. (Genetics 54:61-76, 1966).

a1. for efficient introduction into microorganisms of foreign genetic information:
 (1) hsdR—abolishes restriction, used in $\chi$1776 and $\chi$2076.
 (2) hsdS—abolishes restriction and modification, used in $\chi$1972, $\chi$1976 and other strains being developed and mentioned hereinabove.
 (c) dap and/or asd—abolishes synthesis of diaminopimelic acid (see below) and increases transformability about 3 fold, used in $\chi$1776, $\chi$1972, $\chi$1976 and $\chi$2076.
 (4) Δ[gal-uvrB]—eliminates galactose in lipopolysaccharide in outer membrane (i.e., outer layer of cell wall) and increases transformability 5 to 10 fold (this mutation has other attributes as mentioned below). (galE mutations accomplish the same objective but have not been used in any strains because of the added advantages of using the Δ[gal-uvrB] mutation which deletes the galE gene.) Used in $\chi$1776, $\chi$1972, $\chi$1976 and $\chi$2076.
 (5) endA—eliminates endonuclease I and increases transformability 5 to 10 fold, not used in $\chi$1776 but is used in $\chi$1972, $\chi$1976, $\chi$2076.

a2. for efficient recovery of foreign genetic information from microorganisms:
 (1) dap and asd (see above)—cause cells to be fragile and facilitate their lysis to recover recombinant DNA, used in $\chi$1776 and $\chi$2076 and dap mutations alone in $\chi$1972 and $\chi$1976.
 (2) rfb and oms—when together cause alteration in outer membrane structure causing cells to be more sensitive to lysozyme and detergents used during lysis of cells to recover recombinant DNA, used in $\chi$1776 and $\chi$2076.
 (3) rfa, lpcA and lpcB—when alone or in combination cause alteration in lipopolysaccharide in outer membrane causing cells to be more sensitive to lysozyme and detergents used during lysis of cells to recover recombinant DNA, used in $\chi$1972, $\chi$1976, $\chi$2076.

a3. for expression of foreign genetic information with production of useful products:
 (1) minA+minB—cause production of minicells that lack chromosomal DNA but can possess plasmid vector DNA and thus permit studies on the expression of foreign DNA, present in $\chi$1776 and $\chi$2076. Manipulations necessary to achieve expression of foreign DNA in *E. coli* require development of specific plasmid or phage cloning vectors which in turn requires use of in vitro recombinant DNA molecule construction techniques. Other standard genetic manipulations will have to be done to the host, such as by introducing mutations that block the degradation of foreign proteins (i.e., deg, lon) and permit the "excretion" of foreign proteins outside the cell into the culture medium.

b. for microorganisms to be solely dependent on uniquely defined conditions for their growth and survival:
 (1) dap—abolishes synthesis of diaminopimelic acid, a unique essential ingredient of rigid layer of cell wall which is not found in nature, used in $\chi$1776, $\chi$1972, $\chi$1976 and $\chi$2076.
 (2) asd (Δ[bioH-asd])—also abolishes synthesis of diaminopimelic acid, used in $\chi$1776 and $\chi$2076.
 (3) thyA—abolishes synthesis of thymidine-5'-monophosphate, an essential ingredient of DNA. Cells have to be supplied with either thymidine (which is probably not prevalent in nature) or thymine (which is more prevalent in nature), used in $\chi$1776, $\chi$1972, $\chi$1976 and $\chi$2076.
 (4) deoA—abolishes ability of thyA strains to use low to moderate concentrations of thymine and makes them dependent on thymidine to satisfy requirements of thyA mutation, used in $\chi$1972, $\chi$1976 and $\chi$2076.
 (5) upp—abolishes a minor pathway that permits thyA deoA strains to grow with high concentrations of thymine in the medium. Thus, a strain with thyA deoA and upp mutations is completely dependent on thymidine in the growth medium and thus survives less well in nature than a strain with just the thyA mutation, used in $\chi$1972, $\chi$1976 and $\chi$2076.

c. to preclude establishment or growth or colonization and/or survival of microorganisms under conditions or in ecological niches that are considered to be natural or undesirable habitats:
 (1) dap and asd (see above) in conjunction with mutations such as Δ[gal-uvrB] (used in $\chi$1776, $\chi$1972, $\chi$1976 and $\chi$2076), galE, galU, man and non that abolish colanic acid synthesis precludes long-term survival by causing cell lysis in essentially all environments—natural and unnatural. The rate of death by lysis, however, is dependent on the ability of the environment to support metabolism of microorganisms.
 (2) thyA (as used in $\chi_b$ 1776) plus deoA and upp (as used in $\chi$1972, $\chi$1976 and $\chi$2076) precludes long-term survival in essentially all environments—natural and unnatural. The rate of death, however, is dependent on the ability of the environment to support metabolism of microorganisms.
 (3) rfb and oms (as used in $\chi$1776 and $\chi$2076) confer increased sensitivity to bile, thus preventing survival in the intestinal tract, confer increased sensitivity to detergents that are likely to be encountered in waste water collected by sewerage systems, and cause increased sensitivity to a diversity of drugs, antibiotics, and chemicals that are likely to be encountered in nature as pollutants in waste water collected by sewerage systems and in rivers, lakes, etc. These sensitivities are independent of metabolic activities of cells and should reduce survival in waste water, rivers, etc.

(4) rfa, lpcA and lpcB—when alone or in combination confer same properties as rfb and oms mutations, used in $\chi$1972, $\chi$1976 and $\chi$2076.

(5) Δ[gal-uvrB]—causes microorganism to be inordinately sensitive to ultraviolet light (and thus sunlight), since cells cannot repair UV-induced damage either in dark or in presence of visible light. This property diminishes survival in air, on soil and plants and in surface waters exposed to sunlight and sensitivity is independent of metabolic activity of cells, used in $\chi$1776, $\chi$1972, $\chi$1976 and $\chi$2076.

(6) recA—causes microorganism to be inordinately sensitive to ultraviolet light and chemical mutagens and exposure to same leads to rapid death with concomitant destruction of genetic information, used in $\chi$1976. When used in conjunction with polA(CS) (see below) leads to death with concomitant destruction of genetic information at 32° C. and below even in absence of ultraviolet light and/or chemical mutagens, used in $\chi$1976.

d. to cause genetic information contained in microorganisms to undergo degradation under conditions or in ecological niches that are considered to be natural and/or undesirable habitats of the microorganisms:

(1) thyA—abolishes synthesis of thymidine-5'-monophosphate which is needed for DNA synthesis and in absence of thymine or thymidine causes thymineless death which is associated with concomitant degradation of DNA, used in $\chi$1776.

(2) thyA deoA upp—cause obligate requirement for thymidine which is not prevalent in nature and thus result in more rapid and efficient degradation of genetic information than caused by thyA mutation alone, used in $\chi$1972, $\chi$1976 and $\chi$2076.

(3) polA(CS)—causes DNA polymerase I to be non-functional at temperatures of 32° C. and below (i.e., "cold" sensitive). DNA polymerase I is principally involved in repair of damage to DNA but also plays an important function during DNA synthesis. When the enzyme is non-functional, thymineless death and DNA degradation occur at accelerated rates. This is the first isolation of such cold-sensitive polA mutations, used in $\chi$1972 and $\chi$1976.

(4) recA—abolishes genetic recombination and causes cells to be inordinately sensitive to ultraviolet light (i.e., sunlight) and other chemicals that might be encountered in environment. Exposure to UV, etc., causes rapid degradation of DNA. In conjunction with polA(CS) causes rapid degradation of DNA at 32° C. and below, thus leading to rapid destruction of genetic information in microorganisms that escape to all environments other than within a warm-blooded animal, used in $\chi$1976. The constellation of mutations thyA deoA upp polA(CS) recA as used in $\chi$1976 gives a vast improvement in safety over that afforded by the thyA mutation alone as used in $\chi$1776.

e. to permit cloning vectors used for recombinant DNA molecule research to be dependent on microorganisms for replication, maintenance and/or function:

(1) supE—amber suppressor that rectifies amber nonsense mutations that might be present in viral or plasmid cloning vectors so that their maturation, maintenance, function and/or replication would be dependent on microbial host. It is believed that most microorganisms in nature do not possess amber suppressor mutations. Thus, viral or plasmid cloning vectors could not mature, function and/or replicate in these wild-type microorganisms that might be encountered in nature, used in $\chi$1776, $\chi$1976, and $\chi$2076.

(2) supF (tyrT)—another type of amber suppressor with similar function but different specificity than supE, used in $\chi$1976.

(3) sup$^+$—absence of any and all nonsense suppressor mutations. Permits use of viral vectors that possess amber mutations in genes specifying synthesis of viral structural proteins such as tail proteins so that only non-infectious viral heads containing recombinant DNA are produced. Also permits lysogenization of host with viral vectors possessing amber mutations so that virus maturation is not possible and viral vector maintenance is solely dependent on replication of host chromosome, used in $\chi$1972.

(4) polA(CS)—causes DNA polymerase I not to function at temperatures below 32° C. Certain plasmid cloning vectors, such as ColE1 and its derivatives, are dependent on a functional DNA polymerase I for their vegetative replication. Thus, these plasmids cannot replicate in polA(CS) cells at 32° C. or below and are diluted out (i.e., lost), used in $\chi$1972 and $\chi$1976.

(5) recA—abolishes genetic recombination which is necessary for stable maintenance of λdv plasmid cloning vector, used in $\chi$1976.

f. to preclude or minimize potential or capability of microorganisms to transmit recombinant DNA to other organisms in nature:

All of the mutations cited above that reduce survival of the host microorganism and which lead to degradation of genetic information in other than carefully controlled "laboratory" environments will, of course, limit transmission of recombinant DNA to other organisms. However, some of these mutations as well as others have specific beneficial effects on reducing transmission of recombinant DNA that have not been mentioned above.

(1) thyA—since DNA synthesis is needed for virus cloning vector propagation and since DNA synthesis accompanies and is probably required for conjugational transmission of plasmid DNA, the thyA mutation (as used in $\chi$1776) along with the deoA and upp mutations (as used in $\chi$1972, $\chi$1976 and $\chi$2076) will block DNA synthesis in non-laboratory environments and thus inhibit recombinant DNA transmission.

(2) polA(CS)—functional DNA polymerase I is necessary for the conjugational transmission of the ColE1 cloning vector and its derivatives. Thus, the presence of the polA(CS) mutation minimizes, if not precludes, transmission of recombinant DNA contained on ColE1 vectors at 32° C. and below, used in $\chi$1972 and $\chi$1976.

(3) Δ[gal-uvrB] (used in $\chi$1776, $\chi$1972, $\chi$1976 and $\chi$2076), lps and oms (used in $\chi$1776 and $\chi$2076) and/or rfa, lpcA and/or lpcB (used in $\chi$1972, $\chi$1976 and $\chi$2076)—alter outer membrane of cell and reduce ability of cell to mate with a diversity of different types of donor strains and thus to inherit conjugative plasmids which are necessary for the mobilization and transmission of the non-conjugative (i.e., non-self-transmissible) plamids used as cloning vectors. These mutations also confer resistance to phages D108 and Mu and partical or complete resistance to phage P1, which are generalized transducing phages, thus reducing the probability of transmission of recombinant DNA by transduction. The Δ[gal-uvrB] deletion mutation also eliminates the normal integration sites on the chromosome for the temperate transducing phages λ, 82 and 434.

(4) tonA—confers resistance to phage T1, T5 and φ80 and thus eliminates transductional transmission of recombinant DNA by the transducing phages T1 and φ80, used in $\chi$1776, $\chi$1972, $\chi$1976 and $\chi$2076.

(5) Δ[bioH-asd]—confers resistance to transducing phage λ, used in $\chi$1776 and $\chi$2076.

(6) sup+—absence of any and all nonsense suppressors which prevents production of infectious viral vectors containing recombinant DNA either when the viral vector contains amber nonsense mutations in genes specifying tail proteins or when a viral vector containing amber mutations in any gene specifying viral structural proteins is integrated into, and is therefore dependent upon replication of, host chromosome, used in $\chi$1972.

g. and h. to permit monitoring of microorganisms and minimize likelihood of contamination of microorganisms during recombinant DNA molecule research:

(1) nalA—confers resistance to nalidixic acid. Since nalidixic acid resistance is rare in microorganisms encountered in nature and since the frequency of nalidixic acid resistance mutations is extremely low, the nalA marker can be used to monitor escape and survival of very low numbers of the host microorganism. Nalidixic acid can also be added to cultures during transformation with recombinant DNA to essentially preclude transformation of the contaminating microorganism, used in $\chi$1776, $\chi$1972, $\chi$1976 and $\chi$2076.

(2) cycA and cycB—confer resistance to cycloserine which permits use of cycloserine in place of or in conjunction with nalidixic acid, used in $\chi$1776 and $\chi$2076.

(3) thyA—confers resistance to trimethoprim which premits use of trimethoprim in place of or in conjunction with nalidixic acid and/or cycloserine, used in $\chi$1776, $\chi$1972, $\chi$1976 and $\chi$2076.

MATERIALS AND METHODS USED IN GENETIC MODIFICATION OF MICROORGANISMS

General. All methods are known and are described by Miller (*Experiments in Molecular Genetics*, Cold Spring Harbor Laboratory, 1972) or in the references cited unless otherwise indicated.

Media. Complex media included Penassay broth and agar (Difco; 8 g NaCl/l was added to Penassay agar unless otherwise indicated), L broth (Lennox, 1955), L agar (L broth containing 15 g agar/l except for use with P1L4 in which case 12 g agar/l and $2.5 \times 10^{-3}$M CaCl$_2$ were added), Brain Heart Infusion Broth and Agar (Difco), Tryptone broth (10 g tryptone and 5 g NaCl/l) and agar (Tryptone broth containing 12 g agar/l), EMB agar (Difco EMB Agar Base containing 5 g yeast extract and 5 g NaCl/l) and MacConkey Base Agar (Difco). EMB and MacConkey agars were supplemented with sterile carbon sources to desired concentrations (usually 1%) after autoclaving. L soft agar was L broth containing 6.5 g agar/l.

Synthetic media were ML and MA (Curtiss, 1965) and were supplemented with amino acids, purines, pyrimidines and vitamins at optimal concentrations (Curtiss et al., 1968) and carbon sources to 0.5%. Casamino acids (CAA; Difco) were added at 0.5 or 1.5% as indicated. Thymidine (Thd) or thymine (Thy) was added at 10 μg/ml for complex media and at 40 μg/ml for synthetic media. Biotin (Bio) was used at 0.5 μg/ml and DL-diaminopimelic acid (DAP) at 100 μg/ml, the latter being added to all media and diluents for work with dap mutants. Purine, pyrimidine and vitamin supplements were added to Tryptone broth and agar and MacConkey agar when used for strains that required these compounds.

Buffered saline with gelatin (BSG; Curtiss, 1965) was used as a diluent.

Bacterial strains. The bacterial strains used are listed in Table 1. Gene symbols except for newly identified genes are those used by Bachmann et al. (1976) and most allele numbers have been assigned by the Coli Genetic Stock Center. Allele numbers for certain mutations recently isolated or in strains not previously used have not yet been assigned. Table 2 lists the map positions, if known, for genes used in strain construction. The genealogies of $\chi$1276 (the ancestral parent to $\chi$1776 and $\chi$2076) and $\chi$1038 (the ancestral parent to $\chi$1972 and $\chi$1976) are given in Charts A and B, respectively. The strains were maintained on Penassay agar slants (supplemented with thymidine and/or DAP if necessary) at 4° C. when in routine use and in 1% peptone-5% glycerol (supplemented as above if necessary) at −70° C. for long-term storage.

Bacteriophages. T1, T2, T3, T4, T5, T6, T7, φ12, φ14 and the F⁻ specific phages φII, PV, φW and φH were propagated on *E. coli* B ($\chi$8). λ, 434, 21, φ80 and their derivatives were induced from lysogens or propagated on $\chi$289 or $\chi$1918. S13 was propagated on *E. coli* C ($\chi$695). The F donor-specific phages fl, MS-2, Qβ, R17 and fcanl were propagated on $\chi$1365 and the I donor-specific phage If2 on $\chi$1005. Mu, BF23, P1L4, D108 and K3 were propagated on $\chi$289 as were the rough-specific phages, 6SR, Ffm, Br60, FP1, FP3 and Br10. C21 was propagated on a galE *Salmonella typhimurium* LT2 strain ($\chi$1890). All phages were propagated and assayed using the appropriate media containing the optimal concentrations of Na⁺, Mg⁺⁺ or Ca⁺⁺. Certain of the above-mentioned phages or their derivatives were propagated on other host strains, especially for use in transduction, testing of restriction-modification and suppressor phenotypes, etc. as indicated in the text. General methods for phage work were as described by Adams (1959).

Transduction. P1L4 was propagated on appropriate donor strains. Transduction was accomplished by adding P1L4 to a multiplicity of about 3 per bacteria (actual moi of about one) to recipient bacteria at about $2 \times 10^8$/ml that had grown for 90 to 120 min in L broth containing $2.5 \times 10^{-3}$M CaCl$_2$. After 20 to 30 min at 37° C., samples were plated on appropriate selective media or when phenotypic and/or segregation lag problems were anticipated the culture was diluted 100 to 1000 fold into appropriate liquid media containing $10^{-2}$M citrate and allowed to grow at 37° C. until titers of $10^8$ cells/ml were achieved prior to plating.

Mutagenesis and mutant enrichment techniques. Mutations that were used in strain construction were either spontaneous or induced by nitrous acid, ultraviolet light (UV), nitrosoguanidine or nitrogen mustard. Cell survival following mutagen treatment was always 10 percent or higher to minimize the possibility of multiple mutational events. Introduction of mutations by mutagenesis and/or transduction was usually followed by two cycles of enrichment using 100 μg cycloserine/ml plus 100 μg ampicillin/ml when direct selection for inheritance of the mutation was not possible. Spontaneous thyA mutants were enriched by use of trimethoprim.

Conjugation. Optimal conditions for growing strains to maximize expression of the donor and recipient phenotypes and for carrying out matings were used.

Minicell production. Throughout the construction of $\chi$1776 and $\chi$20761, good minicell-producing isolates were chosen as the derivative of choice. Minicell production was assessed by microscopic examination of late log-phase cultures. The ratio of minicells to normal cells and the frequency of cells in the act of producing minicells were used in determining the choice.

Minicells were purified quantitatively for some experiments by the double sucrose gradient purification technique described by Frazer and Curtiss (1975).

Growth. Conscious selection was made for good growth at each step in the constructions. Growth in various media was monitored spectrophotometrically with all cultures grown and monitored at 37° C.

TABLE 1

Bacterial Strains

| Strain Number | Mating Type | Genotype[a] | Derivation or Source |
|---|---|---|---|
| χ8 | F− | E. coli B prototroph | — |
| χ15 | F+ | supE42 λ− T3r | W1485 (Curtiss, 1964) |
| χ289 | F− | supE42 λ− T3r | χ15 by acridine orange curing (Curtiss et al., 1965) |
| χ487 | F− | leu-6 tonA2 lacY1 tsx-1 supE44 gal-6 λ− his-1 argG6 rpsL104 malT1 xyl-7 mtl-2 metB1 | JC411 (see Bachmann, 1972) |
| χ489 | F− | leu-6 tonA2 lacY1 tsx-1 supE44 gal-6 λ− his-1 recA1 argG6 rpsL104 malT1 xyl-7 mtl-2 metB1 | From χ487 |
| χ509 | F− | supE42 λ− T3r xyl-14 cycB2 cycA1 | Spontaneous from χ323 (Curtiss et al., 1965) |
| χ510 | F− | supE42 λ− his-53 T3r xyl-14 cycB2 cycA1 | UV-induced from χ509 |
| χ520 | F− | tsx-63 supE42 λ− his-53 T3r xyl-14 cycB2 cycA1 | spontaneous from χ510 |
| χ528 | F− | tax-63 supE42 λ− his-53 lysA32 T3r xyl-14 cycB2 cycA1 | UV-induced from χ520 |
| χ536 | Hfr OR11 | supE42 λ− serA12 T3r | Nitrogen mustard-induced from χ493 (Berg and Curtiss, 1967) |
| χ540 | F− | tax-63 purE41 supE42 λ− pyrF30 his-53 T3r xyl-14 cycB2 cycA1 | UV-induced purE from χ529 which was UV-induced pyrF from χ520 (Curtiss et al, 1968) |
| χ559 | Hfr OR11 | leu-45 supE42 λ− ΔthyA57 T3r | Aminopterin selected from χ534 (Berg and Curtiss, 1967) |
| χ569 | F− | tsx-63 supE42 λ− his-53 lysA32 T3r xyl-14 arg-65 cycB2 cycA1 | UV-induced from χ528 |
| χ573 | F′ ORF-4 | F′ lac+ proC+ tsx+ purE+/Δ[lac-purE] supE42 λ− serA12 T3r | From χ536 |
| χ584 | Hfr OR41 | Δ41[pro-lac] supE42 λ− thyA80 T3r cycA1 deo-33 | Spontaneous from χ593 which was derived from χ583 by introduction of F from χ15. χ583 was aminopterin selected from χ354 (Curtiss et al., 1968) |
| χ602 | Hfr OR38 | supE42 λ− T3r | Spontaneous from χ15 (Curtiss et al., 1974) |
| χ656 | F− | thr-16 tsx-63 purE41 supE42 λ− pyrF30 his-53 T3r xyl-14 cycB2 cycA1 | UV-induced from χ540 |
| χ660 | F− | tsx-63 purE41 supE42 λ− pyrF30 his-53 T3r aroB15 xyl-14 cycB2 cycA1 | UV-induced from χ540 |
| χ675 | F− | tsx-63 purE41 supE42 λ− pyrF30 his-53 T3r xyl-14 cycB2 cycA1 serB31 | UV-induced from χ540 |
| χ722 | HfR ORII | supE42 λ− pyr-61 T3r | From E. Goldschmidt |
| χ828 | F− | F-his+/leu-6 lacY1 gal-6 λ− sup-59 his-1 argG6 rpsL104 malT1 xyl-7 mtl-2 metB1 | UV-induced from χ820 (Curtiss et al., 1968) |
| χ832 | F− | thr-16 tsx-63 purE41 supE42 λ− pyrF30 his-53 rpsL97 T3r xyl-14 cycB2 cycA1 | The thr allele was UV-induced in χ540 to yield χ656 and a spontaneous rpsL mutation was selected to give χ723. the proC allele UV-induced to give χ820. |
| χ846 | F− | thr-16 tsx-63 purE41 supE42 λ− pyrF30 his-53 rpsL97, T3r xyl-14 cycB2 cycA1 | UV-induced from χ832 |
| χ849 | F− | thr-16 tonA32 lacY29 proC24 tsx-63 purE41 supE42 λ− pdxC3 pyrF30 his-53 rpsL97 Tr xyl-14 cycB2 cycA1 | Spontaneous from χ846 |
| χ909 | F+ | supE42 (?) λ− dnaB43(TS) | Stallions and Curtiss (1971) |
| χ919 | F− | λ− lysA endA1 met | From J. Hurwitz |
| χ929 | F− | thr-16 car-33 tonA32 lacY29 proC24 tsx-63 purE41 supE42 λ− pdxC3 pyrF30 his-53 rpsL97 T3r xyl-14 cycB2 cycA1 | UV-induced from χ849 |
| χ930 | F− | thr-16 car-33 tonA32 lacY29 proC24 tsx-63 purE41 supE42 λ− pdxC3 pyrF30 his-53 rpsL97 T3r xyl-14 ilv-277 cycB2 cycA1 | UV-induced from χ929 |
| χ961 | F− | thr-16 car-33 tonA32 lacY29 proC24 tsx-63 purE41 supE42 λ− pdxC3 pyrF30 his-53 metC65 rpsL97 T3r xyl-14 ilv-277 cycB2 cycA1 | UV-induced from χ930 |
| χ1005 | R64-11+ | drdII SmrTcr/pro-22 metF63 | From G. Meynell |
| χ1037 | F− | lacY1 supE44 galK2 galT22 metB1 hsdR2 | 802 (Kellenberger et al., 1966; Wood, 1966) |
| χ1038 | F− | lacY1 supE44 galK2 galT22 metB1 hsdS3 | 803 (Kellenberger et al., 1966; Wood, 1966) |

TABLE 1-continued

Bacterial Strains

| Strain Number | Mating Type | Genotype[a] | Derivation or Source |
|---|---|---|---|
| χ1087 | F⁻ | prototroph supF58 (= tyrT58) | From I. P. Crawford as Y mel |
| χ1091 | F⁻ | λ⁻ thyA36 | Derived from W3110 (see Bachmann, 1972) |
| χ1272 | Hfr KL16 | dapD8 λ⁻ relA1 thi-1 | AT986 (Bukhari and Taylor, 1971) |
| χ1365 | Hfr Q13 | rna-19 his-95 tyr-6 relA1 pnp-13 metB1 | Reiner (1969) |
| χ1487 | F⁺ | lacY1 supE44 galK2 galT22 metB1 hsdR2 | χ15 × χ1037 |
| χ1525 | F⁻ | λ⁻ ΔtrpE63 tna | Derived from W3110 (see Bachmann, 1972) |
| χ1634 | F⁻ | thr-16 tsx-63 purE41 supE42 λ⁻ ΔtrpE63 his-53 T3ʳ xyl-14 cycB2 cycA1 | PIL4 (χ1525) transduction of χ656 |
| χ1652 | Hfr G6 | his-323 T3ʳ Δ29[bioH-asd] | From M. Hofnung |
| χ1653 | Hfr AB313 | leu-6 laxZ4 srl-1 rpsL8 mtlA9 thi-1 | From W. Epstein |
| χ1656 | Hfr KL16 | tonA53 dapD8 λ⁻ relA1 thi-1 | Spontaneous from χ1272 |
| χ1674 | Hfr AB313 | leu-6 laxZ4 nalB srl-1 rpsL8 mtlA9 thi-1 | Spontaneous from χ1653 |
| χ1676 | F⁻ | thr-16 tsx-63 purE41 supE42 λ⁻ ΔtrpE63 his-53 T3ʳ xyl-14 metE98 cycB2 cycA1 | PIL4 (χ1108) transduction of χ1634 with ampicillin-cycloserine enrichment |
| χ1692 | F⁻ | thr-16 tsx-63 purE41 supE42 λ⁻ ΔtrpE63 his-53 Teʳ mtlA9 metE98 cycB2 cycA1 | PIL4 (χ1674) transduction of χ1676 |
| χ1707 | F⁻ | leu-6 tonA2 lacY1 tsx-1 gal-6 λ⁻ his-1 supE44 rpsL104 malT1 xyl-7 mtl-2 argG6 metB1 nalB recA1 | Spontaneous from χ489 |
| χ1712 | F⁻ | thr-16 tsx-63 purE41 supE42 λ⁻ ΔtrpE63 his-53 srl-2 T3ʳ mtlA9 metE98 cycB2 cycA1 | UV-induced from χ1692 |
| χ1715 | F⁻ | Δ41[pro-lac] supE42 λ⁻ his-53 T3ʳ xyl-14 cycB2 cycA1 | χ584 × χ510 |
| χ1717 | F⁻ | thr-16 tsx-63 purE41 supE42 λ⁻ ΔtrpE63 his-53 srl-2 nalBʳ T3ʳ mtlA9 metE98 cycB2 cycA1 | Spontaneous from χ1712 |
| χ1753 | F⁻ | tsx-63 supE42 λ⁻ his-53 lysA32 T3ʳ xyl-14 arg-65 | χ722 × χ569 |
| χ1763 | F⁻ | Δ41[pro-lac] supE42 λ⁻ his-53 nalA 13ʳ xyl-14 cycB2 cycA1 | Spontaneous from χ1715 |
| χ1770 | F⁻ | supE42 λ⁻ T3ʳ malT44 | Spontaneous by λvir selection from χ289 |
| χ1795 | F⁻ | supE42 λ⁻ T3ʳ aroB15 | PIL4 (χ660) transduction of χ1770 |
| χ1801 | F⁻ | leu-6 tonA2 lacY1 λ⁻ his-1 non-9 argG6 malT1 xyl-7 mtl-2 metB1 | From E. Siegel |
| χ1821 | Hfr OR11 | supE42 λ⁻ endA1 T3ʳ | PIL4 (χ919) on χ536 |
| χ1825 | F⁻ | supE42 λ⁻ T3ʳ Δ29[bioH-asd] | PIL4 (χ1652) transduction of χ1795 |
| χ1833 | F⁻ | supE42 λ⁻ nalA27 T3ʳ | Spontaneous from χ289 |
| χ1841 | F⁻ | minA1 purE41 supE42 λ⁻ pdxC3 minB2 his-53 nalA28 metC65 rpsL97 T3ʳ xyl-14 ilv-277 cycB2 cycA1 hsdR2 | Spontaneous from χ1488 (see Chart C) |
| χ1857 | F⁻ | leu-6 tonA2 lacY1 λ⁻ non-9 argG6 malT1 xyl-7 mtl-2 metB1 | PIL4 (χ289) transduction of χ1801 |
| χ1890 | F⁻ | Salmonella typhimurium LT-2 met-22 galE409 trpB2 H1-b H2-e,n,x | SL869 from R. T. Jones |
| χ1918 | Hfr H | lacZ (ochre) λ⁻ relA1 rpsL metB1 argE (amber) | SC180 from O. Reyes |
| χ1919 | Hfr H | laxZ (ochre) λ⁻ relA1 rpsL metB1 argE (amber) tyrT | SC183 from O. Reyes |
| χ1922 | F⁻ | supE42 λ⁻ nalA27 ΔthyA57 T3ʳ | PIL4 (χ559) transduction of χ1833 with trimethoprim selection |
| χ1991 | F⁻ | thr-16 tsx-63 purE41 supE42 λ⁻ ΔtrpE63 non-9 srl-2 ΔthyA57 endA1 T3ʳ aroB15 mtlA9 metE98 cycB2 cycA1 | Derived from χ1712 |
| χ2017 | F' | F lac⁺ ΔlacZ trp | R. Goldschmidt |
| χ2050 | F⁻ | thr-16 tsx-63 purE41 supE42 λ⁻ ΔtrpE63 non-9 nalA srl-2 ΔthyA57 endA1 T3ʳ aroB15 mtlA9 metE98 cycB2 cycA1 | Spontaneous nalidixic acid resistant |
| χ2051 | F⁻ | thr-16 tsx-63 purE41 supE42 λ⁻ ΔtrpE63 non-9 nalA dapA or E srl-2 ΔthyA57 endA1 T3ʳ aroB15 mtlA9 metE98 cycB2 cycA1 | Nitrous acid mutagenesis with Amp.-cyc. enrichment from χ2050 |
| χ2055 | F⁻ | thr-16 tsx-63 purE41 supE42 λ⁻ ΔtrpE63 non-9 nalA dap upp srl-2 ΔthyA57 endA1 T3ʳ aroB15 mtlA9 metE98 cycB2 cycA1 | Spontaneous 5′-F-uracil resistant of χ2051 |
| χ2056 | F⁻ | supE42 λ⁻ nalA27 ΔthyA57 T3ʳ ΔdeoA | Nitrous acid mutagenesis of χ1922 |
| χ2057 | F⁻ | thr-16 tsx-63 purE41 supE42 λ⁻ ΔtrpE63 non-9 srl-2 ΔthyA57 endA1 T3ʳ aroB15 mtlA9 metE98 polA(CS) cycB2 cycA1 | Nitrosoguanidine mutagenesis of χ1991 |
| χ2058 | F⁻ | thr-16 tsx-63 purE41 supE42 λ⁻ ΔtrpE63 non-9 srl-2 ΔthyA57 endA1 T3ʳ aroB15 mtlA9 polA(CS) cycB2 cycA1 | PIL4 (χ289) transduction of χ2057 |

[a] Allele numbers have in general been assigned by the Coli Genetic Stock Center.

TABLE 2

Gene Loci Used in Construction of Strains[a]

| Gene Symbol | Map Position (min) | Alternate gene symbols; phenotypic trait affected |
|---|---|---|
| thr | 0.0 | threonine requirement |
| car | 0.6 | arg + ura, cap, pyrA; carbamoylphosphate synthetas |
| ara | 1.3 | utilization of arabinose |
| leu | 1.7 | leucine requirement |
| azi | 2.1 | pea; resistance or sensitivity to sodium azide or phenethyl alcohol; filament formation at 42° C. |
| tonA | 3.45 | resistance to phages T1 and T5 |
| dapD | 3.65 | diaminopimelic acid requirement |
| lpcA | 5.5 | tfrA; defective in synthesis of LPS core and resistance to phages T3, T4, T7, λ and P1 |
| proA | 5.6 | proline requirement |
| lacY | 7.8 | galactose permease (M protein) |
| proC | 8.7 | probably Δ-pyrroline-5-carboxylate reductase |
| tsx | 9.0 | resistant to phage T6 |
| minA | 9.85 | formation of minicells |
| purE | 11.7 | purine requirement |
| rna | 13.8 | rns, rnsA; ribonuclease I |
| con | 14.25 | conjugation deficiency |
| supE | 14.9 | Su II; suppressor of amber mutations |
| galKTEO | 16.7 | utilization of galactose and for galE ability to synthesize colanic acid and incorporate galactose in LPS side chain |
| chlD | 16.8 | resistance to chlorate anaerobically; activation of nitrate reductase by molybdate |
| phr | 16.9 | photoreactivating enzyme |
| attλ,82,434 | 16.95 | integration sites for λ and phages 82 and 434 |
| bioA-D | 17.2 | biotin requirement |
| uvrB | 17.3 | defective in excision repair and UV sensitive |
| chlA | 17.3 | resistace to chlorate anaerobically; effects nitrate reductase and hydrogen lyase activity |
| pdxC | 19.8 | pyridoxine requirement |
| tyrT | 26.7 | supF; tyrosyl-transfer RNA synthetase 1 |
| galU | 26.8 | uridinediphosphoglucose pyrophosphorylase; unable to synthesize colanic acid |
| trpE | 27.4 | anth, tryp-4, tryD; anthranilate synthetase, large subunit |
| pyrF | 27.9 | pyrimidine (uracil) requirement |
| minB | ~29 | formation of minicells |
| his | 44.2 | histidine requirement |
| rfbA,B,D | 44.75 | rough phenotype lacking rhamnose in LPS side chain |
| nalA | 47.95 | resistance to 50-100 μg nalidixic acid/ml |
| dapE | 52.6 | dapB; N-succinyl-diaminopimelate deacylase |
| dapA | 52.65 | dihydrodipicolinate synthetase |
| upp | 53.5 | uraP; uridine monophosphate phosphorylase |
| recA | 57.6 | recH, tif, zab; competence for genetic recombination and repair of radiation damage |
| srl | 57.75 | sorbitol uptake and utilization |
| reiA | 59.2 | RC; regulation of RNA synthesis |
| oms-2 | ~60.2 | outer membrane structure modification |
| thyA | 60.5 | thymidine requirement; thymidylate synthetase |
| lysA | 60.75 | diaminopimelate decarboxylase |
| serA | 62.3 | serine or glycine requirement |
| can | . 62.4 | canavanine resistance |
| endA | 63.2 | DNA specific endonuclease I |
| metC | 63.95 | methionine requirement |
| lpcB | 65 | pon; defective in synthesis of LPS core and resistant to phages T4 and P1 |
| oms-1 | 64–72 | outer membrane structure modification |
| pnp | 67.8 | polynucleotide phosphorylase |
| argG | 67.9 | argininosuccinate synthetase |
| envB | 70.1 | mon; anomalous spheroid cell formation |
| rpsL | 72.05 | str; resistance to streptomycin |
| aroB | 73.45 | shikimic acid requirement |
| bioH | 74.7 | biotin requirement |
| malA | 74.0 | utilization of maltose |
| malT | 74.0 | regulatory gene controlling genes for utilization of maltose and resistance to phage λ |
| asd | 74.3 | requirement of diaminopimelic acid and homoserine (or threonine plus methionine); aspartic acid semialdehyde dehydrogenase |
| xyl | 78.8 | utilization of xylose |
| mtlA | 79.55 | utilization of mannitol; mannitol-semispecific enzyme II of phosphotransferase system |
| rfa | ~80 | defective in LPS core synthesis |
| ilv | 83.2 | isoleucine and valine requirements |
| metE | 84 | met-$B_{12}$; $N^5$-methyltetrahydropteroyl triglutamate-homocysteine methylase |
| polA | 84.95 | resA; DNA polymerase I |
| metB | 87.3 | met-1, met$_l$; cystathionine synthetase |

TABLE 2-continued
Gene Loci Used in Construction of Strains[a]

| Gene Symbol | Map Position (min) | Alternate gene symbols; phenotypic trait affected |
|---|---|---|
| metF | 87.3 | met-2, met₂; $N^5$-$N^{10}$-methylene-tetrahydrofolate reductase |
| thi | 89.0 | requirement for thiamine (Vit $B_1$) |
| dnaB | 91.2 | exrB; groP; DNA synthesis |
| cycB | 93 | resistance to 5-15 μg D-cycloserine/ml; defective in growth on D-alanine or L-alanine |
| cycA | 94 | dagA; resistance to 1.5-3 μg D-cycloserine/ml; defective in transport of D-alanine, D-serine and glycine |
| hsdR | 98.5 | hsr; restriction endonuclease |
| hsdS | 98.5 | hss; site-specific protein for restriction-modification system |
| deoC | 99.45 | dra; thymine uilized efficiently; phosphodeoxyriboaldolase: confers sensitivity to 1 mM thymidine and purine deoxyribonucleosides |
| deoA | 99.46 | tpp; TP; thymidine phosphorylase |
| deoB | 99.5 | drm; thymine utilized efficiently; phosphodeoxyribomutase |
| serB | 99.6 | phosphoserine phosphatase |

[a] Gene symbols and map positions are taken from Bachmann, Low and Taylor (1976). Note that the *E. coli* genetic map has been expanded from 90 min to 100 min.

CHART A
GENEALOGY OF X1276[a]

| | |
|---|---|
| PA678 Str[r] Azi[r] | F⁻ thr-1 ara-13 leu-6 azi-8 tonA2 lacYl supE44 gal-6 λ⁻ minB2 rpsL135 malAl xyl-7 mtl-2 thi-1 |
| ↓ | Triethylenemelamine sel'n. |
| P678-54 | F⁻ thr-1 ara-13 leu-6 azi-8 tonA2 lacYl minAl supE44 gal-6 λ⁻ minB2 rpsL135 malAl xyl-7 mtl-2 thi-1 |
| ↓ | single colony isolated for high minicell production |
| χ925 | F⁻ thr-1 ara-13 leu-6 azi-8 tonA2 lacYl minAl supE44 gal-6 λ⁻ minB2 rpsL135 malAl xyl-7 mtl-2 thi-1 |
| ↓ | X χ909 with sel'n. for Gal⁺ Str[r] recombinants |
| χ911 | F⁺ & F⁻ leu-6 minAl supE42 λ⁻ minB2 rpsL135 malAl xyl-7 mtl-2 thi-1 dnaB43 (TS) |
| ↓ | X χ536 with sel'n. for Thr⁺ Leu⁺ Thi⁺ Ser⁺ recombinants |
| χ964 | F⁺ minAl supE42 λ⁻ minB2 |
| χ961 | F⁻ thr-16 can-33 tonA32 lacY29 proC24 tsx-63 purE41 supE42 λ⁻ pdxC3 pyrF30 his-53 metC65 rpsL97 T3[r] xyl-14 ilv-277 cycB2 cycAl |
| ↓ | X χ964 with sel'n. for Lac⁺ Pyr⁺ Str[r] recombinants |
| χ984 | F⁻ minAl tsx-63 purE41 supE42 λ⁻ pdxC3 minB2 his-53 metC65 rpsL97 T3[r] xyl-14 ilv-277 cycB2 cycAl |
| ↓ | UV treatment |
| χ1276 | F⁻ ara-40 minAl tsx63 purE41 supE42 λ⁻ pdxC3 minB2 his-53 metC65 rpsL97 T3[r] xyl-14 ilv-277 cycB2 cycAl |

[a] PA 678 Str[r] Azi[r] from P678 (see Bachmann, 1972). P678-54 isolated by Adler et al. (1967). Both of these strains are on deposit and available from the Coli Genetic Stock Center, Yale University, New Haven, Connecticut, U.S.A. Other steps in derivation of χ1276 given by Frazer and Curtiss (1975). See Table 1 for origins of χ909, χ536 and χ961.

CHART B
GENEALOGY OF χ1038

| | |
|---|---|
| Arber 101 (C600) | F⁻ thr-1 leu-6 tonA21 lacYl λ⁻ supE44 thi-1 |
| ↓ | X Arber 151 (W4032) Hfr pro-3 lac-3 [DE 6] rel-1 metBl with sel'n. for Thr⁺ Leu⁺ Thi⁺ Pro⁺ |
| Arber 612 | F⁻ lacYl supE44 λ⁻ metBl |
| ↓ | P1 (Arber 144: F⁻ galK2 galT22 malT) with pen. enrichment |
| Arber 704 | F⁻ lacYl supE44 galK2 galT22 λ⁻ metBl |
| ↓ | spontaneous mutation; infection with λdg·B and λcb2; sel'n. of Gal⁻ non-lysogenic segregants |

-continued
CHART B
GENEALOGY OF χ1038

| | |
|---|---|
| Arber 803 | F⁻ supE44 galK2 galT22 λ⁻ metBl hsdS3 |

Arber 803 also called KH803 is χ1038 in the Curtiss *E. coli* collection (see Table 1). The development of Arber 803 and the derivations of Arber 101 and Arber 151 are described by Kellenberger et al. (1966) and Wood (1966).

GENETIC MODIFICATION OF MICROORGANISMS

Construction of χ1776. Chart C gives the genealogy of χ1776 from ₁₀₂1276 (see Chart A). χ1276 was selected as the starting point because it (i) possessed genetic markers that were thought to either be useful in strain construction or provide safety benefits, (ii) had 80 to 90% of its chromosome derived from W1485 and (iii) produced minicells that would be useful in studying expression of plasmid chimeras. The principal goal in constructing $\chi$1776 was to determine whether a given constellation of genetic markers would block cell wall biosynthesis and preclude survival in non-laboratory controlled environments. The goal to maintain isogenicity to W1485 was therefore sacrificed on several occasions for sake of expediency. At each step in the construction, a conscious effort was made to select clones that grew most rapidly and produced the highest yields and purity of minicells.

The first step was to introduce the hsdR2 allele into $\chi$1276 to eliminate the K-12 restriction system and thus enable introduction of foreign DNA sequences into the strain. This was accomplished by conjugation with $\chi$1487, an F+ derivative of $\chi$1037, in a mating of short duration (10 min) with a 1 to 5 donor to recipient ratio so that a high frequency of the Ara+ Str$^r$ recombinants would remain F−. A rapidly growing, high minicell-producing F− Ara+ Str$^r$ recombinant that failed to restrict λvir grown on $\chi$1038 (Table 1) was stocked as $\chi$1488. Since $\chi$1487 is a non-W1485 derived strain, from 3 to 10 minutes of the $\chi$1488 chromosome was replaced with non-W1485 derived information. In the second step, the rpsL97 (str$^r$) allele in $\chi$1488 was removed so that plasmid cloning vectors with Sm$^r$ as a selectable trait could be used in the strain. This was accomplished by conjugation with $\chi$602 (Table 1), a W1485 derived Hfr, to yield $\chi$1678. The removal of the rpsL97 allele in this and other strains was accompanied by a slight but measurable lengthening of the generation time.

The next goal was to abolish the ability of the strain to synthesize the rigid layer of its cell wall in other than carefully controlled laboratory environments. Since diaminopimelic acid (DAP) is a unique constituent of the mucopeptide of the rigid layer of the cell wall in most gram-negative bacteria and since DAP is not known to be synthesized by eukaryotic organisms, it was considered that free DAP should not be prevalent in nature and therefore that Dap− mutants should undergo lysis and not survive in nature. After screening numerous dap alleles for genetic stability, the dapD8 marker which was induced by nitrosoguanidine was selected as the least revertable (ca. $10^{-9}$ revertant frequency) for introduction into $\chi$1678. This was accomplished by contransduction of dapD8 with the tonA53 marker (90% cotransducible). $\chi$1678 was permitted to grow in L broth+DAP for 9 generations following transduction with P1L4 ($\chi$1656) before challenging with a high multiplicity of T5. The introduction of the dapD8 allele into $\chi$1678 to yield $\chi$1697 was accompanied by a lesion conferring thermosensitivity which was later found to be present in $\chi$1656 and some but not all of the T5$^r$ dapD8 transductants obtained from $\chi$1678. This TS defect was eliminated by spontaneous reversion to yield $\chi$1702.

$\chi$1702 was subjected to numerous tests with disappointing results. It did not undergo an appreciable frequency of DAP-less death in L broth, Penassay broth or ML (with or without Casamino acids) that lacked DAP and actually could grow in these media. It also survived passage through the intestinal tract of the rat (see later) and was a proficient recipient in matings with R+ donors. The initial belief was that the dapD8 allele was not only revertable but leaky. A search for other stable mutations conferring a Dap− phenotype was therefore initiated while continuing studies on the properties of $\chi$1702. It was soon observed that $\chi$1702 did undergo DAP-less death at 42° C. in all media lacking DAP and that it could form colonies on L and Penassay agars lacking DAP at 30° and 37° C. but not at 42° C. These colonies were mucoid. By replica plating tests it was determined that the number of colonies which replicated to media without DAP increased as the DAP concentration in the master plates decreased. It was also observed that the omission of NaCl from the L or Penassay agar lacking DAP precluded colony formation and that in liquid media lacking DAP the omission of NaCl also led to better rates of DAP-less death and inability of $\chi$1702 to grow in the absence of DAP. It was then determined that the ability of $\chi$1702 to grow in liquid media containing NaCl but lacking DAP was due to the formation of spheroplasts that were surrounded by a mucopolysaccharide capsule which must act as a stabilizer against the osmotic pressure differences between the cell cytoplasm and the surrounding medium. The mucoid colonies forming on solid media lacking DAP were also composed of capsule surrounded spheroplasts. By this time it appeared certain that $\chi$1702 and some other Dap− strains were producing colanic acid whose synthesis is (i) regulated by the lon (capR) gene, (ii) prevented by incubation at 42° C. and (iii) stimulated by presence of NaCl and adverse environments during cell growth. It thus became apparent that it would be necessary to eliminate the ability to produce colanic acid to obtain a strain that could neither synthesize a cell wall nor survive in other than carefully controlled laboratory environments.

During these studies, $\chi$1702 was manipulated in three steps (Chart C) to give rise to $\chi$1845 which possesses the Δ29[bioH-asd] deletion which also confers a Dap− phenotype because of the inability to synthesize homoserine semialdehyde. $\chi$1845, like $\chi$1702, can produce colanic acid and survive in the absence of DAP under the appropriate conditions although it is unable to revert to Dap+. A spontaneous high-level nalidixic acid resistant mutant was selected to facilitate retrival of the strain during rat feeding tests. This was done by plating a concentrated $\chi$1845 culture on L agar containing DAP and 100 µg nalidixic acid/ml. 1846 presumably has a mutation in the nalA gene since this is the only locus known in which mutations confer high-level resistance to nalidixic acid. $\chi$1846 was then mutagenized by nitrous acid treatment and after sufficient growth to permit segregation and expression, was plated on MacConkey agar containing DAP, adenine, galactose, and 0.2% KCLO$_3$. These plates were incubated anaerobically in a BBL Gas-Pak jar to obtain Gal− Chl$^r$ mutants that would be unable to synthesize colanic acid. The Δ40[gal-uvrB] deletion induced in $\chi$1846 to yield $\chi$1849 does block colanic acid synthesis and at the same time confers high UV sensitivity, abolishes photoreactivation and diminishes lysogenization by λ, 82 and 434. $\chi$1849 was shown to be unable to survive in the absence of DAP and exhibited good rates of DAP-less death although it still could survive passage through the rat intestine and was proficient as a recipient for some but not all conjugative R plasmids. It was thus decided to remove the his-53, purE41 and ilv-277 alleles since they might tend to reduce growth rates in non-laboratory environments and thus diminish either the rates or likelihood of DAP-less death. It should be noted that although studies in mice some ten years ago indicated that pur mutations were detrimental to bacterial survival and/or colonization of the intestinal tract (Jones and Curtiss, unpublished), such effects with pur⁻ strains were not observed in experiments in which strains were fed to rats.

Concomitant with the removal of the his-53 allele to yield $\chi$1855, another mutation was introduced that results in sensitivity to bile salts and detergents, increases sensitivity to numerous antibiotics, alters phage sensitivity patterns and reduces recipient ability in matings with donors possessing several different R plasmid types. It is believed that this lesion is in either the rfbA or rfbB locus both of which are cotransducible with the his locus. The basis for this belief as well as the dependence of the phenotype due to this mutation on the presence of at least one additional mutation in $\chi$1849 that is designated oms-1 has been substantiated. The combined effects of the rfb-2 and oms-1 mutations also result in a Con⁻ recipient phenotype, increased resistance to various phages and sensitivity to bile salts, antibiotics, etc. $\chi$1855 and its descendants are also thermosensitive, being unable to form colonies at 42° C. $\chi$1849 and its ancestors (except for $\chi$1697) plate normally at 42° C.

The removal of the purE41 and ilv-277 alleles by transduction with P1L4 ($\chi$289) to yield $\chi$1864 (Chart C) was accomplished without great difficulty. It should be mentioned that although $\chi$1855 and $\chi$1859 were partially resistant to P1L4 due to the oms-1 and rfb-2 mutations introduced into $\chi$1849 and $\chi$1855, the transducibility of these strains was only reduced 5- to 10-fold compared to $\chi$1849 and the frequencies of Ilv⁺ and Pur⁺ transductants were still far in excess of the reversion frequencies.

Since thyA mutations lead to thymineless death and degradation of DNA in media lacking thymine and diminish survival of strains during passage through the rat intestine, it was decided to introduce the thyA57 mutation from $\chi$559 (Table 1) into $\chi$1864 as the last step in constructing $\chi$1776. The thyA57 allele was selected since it has never been observed to revert either in $\chi$559 or in any other strain into which the allele had been introduced. However, the introduction of this mutation into 1864 proved to be difficult and probably was not in reality achieved. After permitting 30 minutes for P1L4 ($\chi$559) adsorption to $\chi$1864 in L broth+DAP+2.5×10⁻³M CaCl₂, the mixture was both plated on MA+Thr, Met, DAP, Bio, Thd, Glucose containing 10 μg trimethoprim/ml and diluted into L broth+Thd+DAP+10⁻²M citrate (1 ml into 9 ml) to allow growth for segregation and expression. After growth to about 2×10⁸ cells/ml samples were plated on selective media and another 1 to 10 dilution was made into L broth+Thd+DAP+10⁻²M citrate. The plating, dilution, incubation and final plating were repeated once more. The frequencies of colonies appearing on selective media were 1.2×10⁻⁶, 7.0×10⁻⁷, 1.3×10⁻⁶ and 1.8×10⁻⁶ for the immediate plating and following growth of the first, second and third diluted mixtures. The percentages of thermosensitive Thy⁻ clones were 40, 29, 21 and 11 for the four platings. In addition, the trimethoprimresistant colonies grew up after 3 days incubation for the first two platings whereas only 2 days incubation were required for the last two platings. Since about half of spontaneous Thy⁻ mutants are thermosensitive for their thymine requirement (i.e., they grow at 30° C. without thymine) and since transductant colonies should grow faster than colonies arising from spontaneous mutations occurring on the plates, the non-thermosensitive clones appearing from the last two platings were believed to represent successful thyA57 transductants. One of these was designated $\chi$1776. Subsequently, it was discovered that $\chi$1776 as well as several other of these non-thermosensitive thyA clones were able to revert to Thy⁺ at a very low frequency thus casting doubt on the belief that the thyA mutation in $\chi$1776 is the thyA57 allele which may indeed be a composite of two mutations in the thyA gene, only one of which was introduced into $\chi$1776. $\chi$1776 is also less able to grow at 42° C. than $\chi$1864 and possesses at least one additional mutation that alters the structure of the outer membrane and contributes to bile sensitivity, phage resistance and the Con⁻ recipient phenotype. This mutation designated oms-2 is about 65 to 80 percent cotransducible with thyA.

CHART C
GENEALOGY OF $\chi$1776

| | |
|---|---|
| $\chi$1276 | F⁻ ara-40 minA1 purE41 supE42 λ⁻ pdxC3 minB2 his-53 metC65 rpsL97 T3ʳ xyl-14 ilv-277 cycB2 cycA1 |
| ↓ | X $\chi$1487 with sel'n. for Ara⁺ Strʳ to introduce hsdR2 allele |
| $\chi$1488 | F⁻ minA1 purE41 supE42 λ⁻ pdxC3 minB2 his-53 metC65 rpsL97 T3ʳ xyl-14 ilv-277 cycB2 cycA1 hsdR2 |
| ↓ | X $\chi$602 with sel'n. for Xyl⁺ Cycʳ to eliminate rpsL97 allele |
| $\chi$1678 | F⁻ minA1 purE41 supE42 λ⁻ pdxC3 minB2 his-53 metC65 T3ʳ ilv-277 cycB2 cycA1 hsdR2 |
| ↓ | P1L4 ($\chi$1656) with T5 sel'n. to cotransduce in dapD8 allele; with concomitant loss of pdxC3 |
| $\chi$1697 | F⁻ tonA53 dapD8 minA1 purE41 supE42 λ⁻ minB2 his-53 metC65 T3ʳ ilv-277 cycB2 cycA1 hsdR2 (contains TS mutation linked to dapD8 that prevents growth at 42° C. but not at 37° C.) |
| ↓ | spont. sel'n. at 42° C. to eliminate TS defect |
| $\chi$1702 | F⁻ tonA53 dapD8 minA1 purE41 supE42 λ⁻ minB2 his-53 metC65 T3ʳ ilv-277 cycB2 cycA1 hsdR2 |
| ↓ | λvir sel'n. to obtain malT derivative |
| $\chi$1777 | F⁻ tonA53 dapD8 minA1 purE41 supE42 λ⁻ minB2 his-53 metC65 T3ʳ malT43 ilv-277 cycB2 cycA1 hsdR2 |
| ↓ | P1L4 ($\chi$660) with sel'n. for Mal⁺ and Aro⁻ to introduce aroB15 allele |
| $\chi$1820 | F⁻ tonA53 dapD8 minA1 purE41 supE42 λ⁻ minB2 his-53 metC65 T3ʳ aroB15 ilv-277 cycB2 cycA1 hsdR2 P1L4 ($\chi$1825) with sel'n. for Aro⁺ to introduce Δ29[bioH-asd] deletion |
| $\chi$1845 | F⁻ tonA53 dapD8 minA1 purE41 supE42 λ⁻ minB2 his-53 |

-continued

CHART C
GENEALOGY OF χ1776

|  |  |
|---|---|
|  | metC65 T3$^r$ Δ29[bioH-asd] ilv-277 cycB2 cycA1 hsdR2 |
| ↓ | spont. sel'n. for resistance to 100 μg nalidixic acid/ml |
| χ1846 | F$^-$ tonA53 dapD8 minA1 purE41 supE42 λ$^-$ minB2 his-53 nalA25 metC65 T3$^r$ Δ29[bioH-asd] ilv-277 cycB2 cycA1 hsdR2 |
| ↓ | nitrous acid mutagenesis and sel'n. for anerobic chlorate resistance on MacConkey-Gal agar accompanied by introduction of oms-1 mutation |
| χ1849 | F$^-$ tonA53 dapD8 minA1 purE41 supE42 Δ40[gal-uvrB]λ$^-$ minB2 his-53 nalA25 metC65 oms-1 T3$^r$ Δ29[bioH-asd] ilv-277 cycB2 cycA1 hsdR2 |
| ↓ | P1L4 (χ289) with sel'n. for His$^+$ with concomitant change to Con$^-$, bile salts sensitivity and TS phenotype |
| χ1855 | F$^-$ tonA53 dapD8 minA1 purE41 supE42 Δ40[gal-uvrB] λ$^-$ minB2 rfb-2 nalA25 metC65 oms-1 T3$^r$ Δ29[bioH-asd] ilv-277 cycB2 cycA1 hsdR2 |
| ↓ | P1L4 (χ289) with sel'n. for Pur$^+$ |
| χ1859 | F$^-$ tonA53 dapD8 minA1 supE42 Δ40[gal-uvrB] λ$^-$ minB2 rfb-2 nalA25 metC65 oms-1 T3$^r$ Δ29[bioH-asd] ilv-277 cycB2 cycA1 hsdR2 |
| ↓ | P1L4 (χ289) with sel'n. for Ilv$^+$ |
| χ1864 | F$^-$ tonA53 dapD8 minA1 supE42 Δ40[gal-uvrB] λ$^-$ minB2 rfb-2 nalA25 metC65 oms-1 T3$^r$ Δ29[bioH-asd] cycB2 cycA1 hsdR2 |
| ↓ | P1L4 (χ559) with trimethoprim sel'n. to introduce thyA57 allele with presumed concomitant introduction or expression of an additional mutation affecting outer membrane structure |
| χ1776 | F$^-$ tonA53 dapD8 minA1 supE42 Δ40[gal-uvrB] λ$^-$ minB2 rfb-2 nalA25 oms-2 thyA57* metC65 oms-1 T3$^r$ Δ29[bioH-asd] cycB2 cucA1 hsdR2 |

χ1849 through χ1776 are phenotypically T3 sensitive. The designation thyA57* used in the χ1776 genotype is to indicate that this thyA mutation which reverts may not have been derived from the non-reverting thyA57 mutation in χ559.

Construction of χ2076. During the testing of χ1776, it became apparent that both thyA$^+$ and bile salts resistant revertants were obtained at very low but measurable frequencies. In other studies it was learned that the endA1 mutation increased transformability of strains 5 to 10 fold and that the combination thyA deoA upp precluded growth of strains on thymine and resulted in improved rates of thymineless death. It was therefore decided to construct an improved derivative of χ1776 designated χ2076 (see Chart D).

The steps involved in constructing χ2076 are straightforward. The removal of the thyA57* mutation with the introduction of the lysA32 mutation was associated with some difficulty, however, since some of these cotransductants presumably became oms-2$^+$ and thereby somewhat bile salts resistant. Also some of these cotransductants that retained bile salts sensitivity became completely resistant to P1L4 thus precluding further use of P1 transduction for strain construction. For this reason, a thy$^+$ lysA32 cotransductant that still exhibited sensitivity to P1 was selected and this strain (χ2065) was transduced to lysA$^+$ thyA57 to yield χ2067. The thyA57 mutation in this strain has not been observed to revert to thyA$^+$.

The introduction of the serA12 allele to permit contransduction of serA$^+$ and endA1 and of the serB31 allele to permit introduction of serB$^+$ and ΔdeoA utilizes the ampicillin-cycloserine enrichment technique following P1L4 transduction and a period of growth under permissive conditions to permit segregation and phenotypic expression.

upp mutations confer resistance to 5'-fluorouracil and therefore can be selected as spontaneous mutations with subsequent testing of mutants by standard techniques to verify that the resistance to 5'-fluoro-uracil is due to an upp mutation. The selection of spontaneous mutations for resistance to phage K3 which results in alteration of outer membrane protein 3a and a Con$^-$ recipient phenotype in matings with donors possessing F-type plasmids and for resistance to phage T4 which results in mutations in the lpcA or lpcB genes and confers bile salts sensitivity are easily accomplished. However, the fact that χ1776 is already Con$^-$ and bile salts sensitive complicates the genetic and phenotypic analysis of strains with additional mutations affecting these properties. Although non-revertability of the bile sensitivity trait and decreased recipient ability compared to χ1776 will be testable attributes of χ2076, the complete resistance of this strain to transducing phages and the inability to use conjugational analyses will essentially preclude a genetic analysis to determine which genes have been rendered defective by mutational lesions.

CHART D
GENEALOGY OF χ2076

|  |  |
|---|---|
| χ1776 | F$^-$ tonA53 dapD8 minA1 supE42 Δ40[gal-uvrB] λ$^-$ minB2 rfb-2 nalA25 oms-2 thyA57* metC65 oms-1 Δ29[bioH-asd] cycB2 cycA1 hsdR2 |
| ↓ | P1L4 (χ1753) with sel'n. for thyA$^+$ |
| χ2065 | F$^-$ tonA53 dapD8 minA1 supE42 Δ40[gal-uvrB] λ$^-$ minB2 rfb-2 nalA25 oms-2 lysA32 metC65 oms-1 Δ29[bioH-asd] cycB2 cycA1 hsdR2 |
| ↓ | P1L4 (χ559) with sel'n. for lysA$^+$ |

-continued

CHART D
GENEALOGY OF χ2076

| | |
|---|---|
| χ2067 | F$^-$ tonA53 dapD8 minA1 supE42 Δ40[gal-uvrB] λ$^-$ minB2 rfb-2 nalA25 oms-2 ΔthyA57 metC65 oms-1 Δ29[bioH-asd] cycB2 cycA1 hsdR2 |
| ↓ | P1L4 (χ573) with Amp-Cyc enrichment |
| χ2068 | F$^-$ tonA53 dapD8 minA1 supE42 Δ40[gal-uvrB] λ$^-$ minB2 rfb-2 nalA25 oms-2 ΔthyA57 serA12 metC65 oms-1 Δ29[bioH-asd] cycB2 cycA1 hsdR2 |
| ↓ | P1L4 (χ1821) with sel'n. for serA$^+$ |
| χ2069 | F$^-$ tonA53 dapD8 minA1 supE42 Δ40[gal-uvrB] λ$^-$ minB2 rfb-2 nalA25 oms-2 ΔthyA57 endA1 metC65 oms-1 Δ29[bioH-asd] cycB2 cycA1 hsdR2 |
| ↓ | P1L4 (χ675) with Amp-Cyc enrichment |
| χ2070 | F$^-$ tonA53 dapD8 minA1 supE42 Δ40[gal-uvrB] λ$^-$ minB2 rfb-2 nalA25 oms-2 ΔthyA57 endA1 metC65 oms-1 Δ29[bioH-asd] cycB2 cycA1 hsdR2 serB31 |
| ↓ | P1L4 (χ2056) with sel'n. for serB$^+$ |
| χ2071 | F$^-$ tonA53 dapD8 minA1 supE42 Δ40[gal-uvrB] λ$^-$ minB2 rfb-2 nalA25 oms-2 ΔthyA57 endA1 metC65 oms-1 Δ29[bioH-asd] cycB2 cycA1 hsdR2 ΔdeoA |
| ↓ | spont. 5'-F-uracil resistance |
| χ2073 | F$^-$ tonA53 dapD8 minA1 supE42 Δ40[gal-uvrB] λ$^-$ minB2 rfb-2 nalA25 upp oms-2 ΔthyA57 endA1 metC65 oms-1 Δ29[bioH-asd] cycB2 cycA1 hsdR2 ΔdeoA |
| ↓ | spont. sel'n. for K3$^r$ |
| χ2074 | F$^-$ tonA53 dapD8 minA1 supE42 Δ40[gal-uvrB] λ$^-$ minB2 rfb-2 nalA25 upp oms-2 ΔthyA57 endA1 con metC65 oms-1 Δ29[bioH-asd] cycB2 cycA1 hsdR2 ΔdeoA |
| ↓ | spont. sel'n. for T4$^r$ |
| χ2076 | F$^-$ tonA53 dapD8 minA1 supE42 Δ40[gal-uvrB] λ$^-$ minB2 rfb-2 nalA25 upp oms-2 ΔthyA57 endA1 con metC65 oms-1 Δ29[bioH-asd] cycB2 cycA1 hsdR2 ΔdeoA 1pcA or 1pcB or rfa |

Construction of χ1972 and χ1976. Although χ1776 and χ2076 are suitable safer hosts for use with plasmid cloning vectors in recombinant DNA molecule research, they are resistant to bacteriophage λ and are therefore not particularly useful in conjuction with λ-derived cloning vectors. For this reason and because the production of minicells is less important for experiments with λ cloning vectors, a series of strains was designed to facilitate use with these vectors as well as with plasmid cloning vectors. Chart E gives the genealogies of χ1972 and χ1976. The design and construction was based on findings and techniques described hereinabove. In addition to χ1972 and χ1976, strains χ1961, χ1963, χ1966, χ1968, χ1969, χ1970, χ1973, χ1974 and χ1975 derived during their construction have utility for use with particular types of phage and plasmid cloning vectors.

CHART E
GENEALOGIES OF χ1972 AND χ1976

| | |
|---|---|
| χ1038 | F$^-$ lacY1 supE44 galK2 galT22 λ$^-$ metB1 hsdS3 |
| ↓ | P1L4 (χ289) with sel'n. for Gal$^+$ |
| χ1947 | F$^-$ lacY1 supE44 λ$^-$ metB1 hsdS3 |
| ↓ | spont. with anaerobic sel'n. for Gal$^-$ Chl$^r$ |
| χ1948 | F$^-$ lacY1 supE44 Δ[gal-uvrB] λ$^-$ metB1 hsdS3 |
| ↓ | spont. resistance to 50 μg nalidixic acid/ml |
| χ1949 | F$^-$ lacY1 supE44 Δ40[gal-uvrB] λ$^-$ nalA metb1 hsdS3 |
| ↓ | P1L4 (χ559) with trimethoprim sel'n. |
| χ1950 | F$^-$ lacY1 supE44 Δ[gal-uvrB] λ$^-$ nalA ΔthyA57 metB1 hsdS3 |
| ↓ | P1L4 (χ289) with sel'n. for metB$^+$ |
| χ1952 | F$^-$ lacY1 supE44 Δ[gal-uvrB] λ$^-$ nalA ΔthyA57 hsd53 |
| ↓ | P1L4 (χ1702) with sel'n. for T5$^r$ |
| χ1953 | F$^-$ tonA53 dapD8 lacY1 supE44 Δ[gal-uvrB] λ$^-$ nalA ΔthyA57 hsdS3 |
| ↓ | P1L4 (χ573) with Amp.-Cyc. enrichment |
| χ1954 | F$^-$ tonA53 dapD8 lacY1 supE44 Δ[gal-uvrB] λ$^-$ nalA ΔthyA57 serA12 hsdS3 |
| ↓ | P1L4 (χ1821) with sel'n. for serA$^+$ |
| χ1955 | F$^-$ tonA53 dapD8 lacY1 supE44 Δ[gal-uvrB] λ$^-$ nalA ΔthyA57 endA1 hsdS3 |
| ↓ | P1L4 (χ289) with sel'n. for lacY$^+$ |
| χ1956 | F$^-$ tonA53 dapD8 supE44 Δ]gal-uvrB] λ$^-$ nalA ΔthyA57 endA1 hsdS3 |
| ↓ | P1L4 (χ2017) with Amp.-Cyc. enrichment |
| χ1957 | F$^-$ tonA53 dapD8 ΔlacZ supE44 Δ[gal-uvrB] λ$^-$ nalA ΔthyA57 endA1 hsdS3 |
| ↓ | P1L4 (χ675) with Amp.-Cyc. enrichment |
| χ1958 | F$^-$ tonA53 dapD8 ΔlacZ supE44 Δ[gal-uvrB] λ$^-$ nalA ΔthyA57 endA1 hsdS3 serB31 |
| ↓ | P1L4 (χ2056) with sel'n. for serB$^+$ |
| χ1959 | F$^-$ tonA53 dapD8 ΔlacZ supE44 Δ[gal-uvrB] λ$^-$ nalA |

-continued

CHART E
GENEALOGIES OF χ1972 AND χ1976

| | ΔthyA57 endA1 hsdS3 ΔdeoA |
|---|---|
| ↓ | P1L4 (χ2055) with sel'n. for 5'-F-uracil resistance |
| χ1960 | F⁻ tonA53 dapD8 ΔlacZ supE44 Δ[gal-uvrB] λ⁻ nalA dapA or E upp ΔthyA57 endA1 hsdS3 ΔdeoA |
| | ↓ P1L4 (χ1091) with sel'n. for resistance to λvir N N |
| | χ1961 F⁻ tonA53 dapD8 ΔlacZ Δ[gal-uvrB] λ⁻ nalA dapA or E upp ΔthyA57 endA1 hsdS3 ΔdeoA |
| ↓ | P1L4 (χ1525) with Amp.-Cyc. enrichment |
| χ1962 | F⁻ tonA53 dapD8 ΔlacZ supE44 Δ[gal-uvrB] λ⁻ ΔtrpE63 nalA dapA or E upp ΔthyA57 endA1 hsdS3 ΔdeoA |
| | ↓ P1L4 (χ1087) with sel'n. for Trp⁺ |
| | χ1963 F⁻ tonA53 dapD8 ΔlacZ supE44 Δ[gal-uvrB] λ⁻ supF58 nalA dapA or E upp ΔthyA57 endA1 hsdS3 ΔdeoA |
| ↓ | P1L4 (χ1674) with Amp.-Cyc. enrichment |
| χ1964 | F⁻ tonA53 dapD8 ΔlacZ supE44 Δ[gal-uvrB] λ⁻ ΔtrpE63 nalA dapA or E upp ΔthyA57 endA1 mtlA9 hsdS3 ΔdeoA |
| ↓ | P1L4 (χ1108) with Amp.-Cyc. enrichment |
| χ1965 | F⁻ tonA53 dapD8 ΔlacZ supE44 Δ[gal-uvrB] λ⁻ ΔtrpE63 nalA dapA or E upp ΔthyA57 endA1 mtlA9 metE98 hsdS3 ΔdeoA |
| ↓ | P1L4 (χ2058) with sel'n. for met⁺ |
| χ1966 | F⁻ tonA53 dapD8 ΔlacZ supE44 Δ[gal-uvrB] λ⁻ ΔtrpE63 nalA dapA or E upp ΔthyA57 endA1 mtlA9 polA(CS) hsdS3 ΔdeoA |
| ↓ | P1L4 (χ1717) with Amp.-Cyc. enrichment |
| χ1967 | F⁻ tonA53 dapD8 ΔlacZ supE44 Δ[gal-uvrB] λ⁻ ΔtrpE63 nalA dapA or E upp srl-2 ΔthyA57 endA1 mtlA9 polA(CS) hsdS3 ΔdeoA |
| | ↓ P1L4 (χ1091) with sel'n. for resistance to λvir N |
| | χ1969 F⁻ tonA53 dapD8 ΔlacZ Δ[gal-uvrB] λ⁻ ΔtrpE63 nalA dapA or E upp srl-2 ΔthyA57 endA1 mtlA9 polA(CS) hsdS3 ΔdeoA |
| | ↓ spont. sel'n. for K3ʳ |
| | χ1970 F⁻ tonA53 dapD8 ΔlacZ Δ[gal-uvrB] λ⁻ ΔtrpE63 nalA dapA or E upp srl-2 ΔthyA57 endA1 con mtlA9 polA(CS) hsdS3 ΔdeoA |
| | ↓ spont. sel'n. for T4ʳ |
| | χ1972 F⁻ tonA53 dapD8 ΔlacZ Δ[gal-uvrB] λ⁻ ΔtrpE63 nalA dapA or E upp srl-2 ΔthyA57 endA1 con mtlA9 polA(CS) hsdS3 ΔdeoA lpcA or lpcB or rfa |
| ↓ | P1L4 (χ1087) with sel'n. for trp⁺ |
| χ1968 | F⁻ tonA53 dapD8 ΔlacZ supE44 Δ[gal-uvrB] λ⁻ supF58 nalA dapA or E upp srl-2 ΔthyA57 endA1 mtlA9 polA(CS) hsdS3 ΔdeoA |
| ↓ | P1L4 (χ1707) with sel'n. for srl⁺ |
| χ1973 | F⁻ tonA53 dapD8 ΔlacZ supE44 Δ[gal-uvrB] λ⁻ supF58 nalA dapA or E upp recA1 ΔthyA57 endA1 mtlA9 polA(CS) hsdS3 ΔdeoA |
| ↓ | spont. sel'n. for K3ʳ |
| χ1974 | F⁻ tonA53 dapD8 ΔlacZ supE44 Δ[gal-uvrB] λ⁻ supF58 nalA dapA or E upp recA1 ΔthyA57 endA1 con mtlA9 polA(CS) hsdS3 ΔdeoA |
| ↓ | spont. sel'n. for T4ʳ |
| χ1975 | F⁻ tonA53 dapD8 ΔlacZ supE44 Δ[gal-uvrB] λ⁻ supF58 nalA dapA or E upp recA1 ΔthyA57 endA1 con mtlA9 polA(CS) hsdS3 ΔdeoA lpcA or lpcB or rfa |
| ↓ | spont. sel'n. for T3ʳ T7ʳ |
| χ1976 | F⁻ tonA53 dapD8 ΔlacZ supE44 Δ[gal-uvrB] λ⁻ supF58 nalA dapA or E upp recA1 ΔthyA57 endA1 con mtlA9 polA(CS) hsdS3 ΔdeoA lpcA and/or lpcB and/or rfa |

A deposit of χ1038 has been made with the American Type Culture Collection, Rockville, Maryland, U.S.A. and has been assigned ATCC No. 31246.

METHODS USED AND RESULTS OF TESTING GENOTYPIC AND PHENOTYPIC PROPERTIES OF MICROORGANISMS WITH SPECIAL REFERENCE TO χ1776 AS AN EXAMPLE

Materials and Methods

General. The media, bacteriophages and bacterial strains (see Table 1), and the methods for transduction, mutagenesis and mutant enrichment, conjugation, mini- cell production and growth were described hereinabove. Table 3 lists the strains possessing conjugative plasmids that were used to test the recipient ability of χ1776 under various conditions and to investigate the mobilization and transmission of non-conjugative plasmid cloning vectors such as pSC101, pMB9 and pCR1 in biparental and triparental matings.

Survival. Ability of cells to give rise to colonies as a function of time under various non-permissive conditions were measured by plating appropriate dilutions on media that were optimal for the recovery and growth of $\chi 1776$ or its plasmid-containing derivatives.

Labelling and isolation of DNA. Cells were labelled with [$^3$H]thymidine using standard methods. Plasmid DNA was isolated by using the cleared lysate procedure and/or the ethidium bromide-CsCl procedure. Plasmid DNA from minicells was isolated and analysed by alkaline and neutral sucrose gradient centrifugation. Alkaline sucrose gradients were also used to evaluate breakdown of chromosomal DNA.

Determination of radioactivity. Samples containing radioactively labelled DNA were placed on Whatman 3 MM filters and the DNA was precipitated with trichloracetic acid. Radioactivity was determined in a Beckman Model LS-230 liquid scintillation counter using a BBOT-toluene scintillation fluid in minivials.

Transformation. The method described by Lederberg and Cohen (1974) was initially used to transform strains with plasmid DNA although these methods are unsatisfactory for $\chi 1776$ and other strains with mutations altering the outer membrane structure. A new method for transformation of such strains has therefore been developed as described hereinafter. pSC101 plasmid DNA was used to transform $\chi 1776$ to yield $\chi 1876$ which has been tested in comparison to $\chi 1776$ to verify that the presence of a plasmid cloning vector does not alter the utility or safety properties of $\chi 1776$. More limited tests have been performed with $\chi 1776$ derivatives transformed with pMB9 DNA ($\chi 2042$) and pCR1 DNA ($\chi 2043$).

Other Methods. Methods that are unique to a particular experiment are described in conjunction with that experiment. When not otherwise indicated incubations were at 37° C.

Results

Genotypic and Phenotypic Characterization of Strains

Phenotypes associated with mutations in $\chi 1776$. The phenotypic properties of $\chi 1776$ and the listing of mutations responsible for each trait are given in Table 4.

Stability of genotypic and phenotypic traits. Data on the reversion of various mutational markers in $\chi 1776$ and $\chi 1876$ are presented in Table 5. As expected those traits that are due to deletions and/or to two mutational lesions do not revert. Actually most of these traits have been checked for stability in some of $\chi 1776$'s ancestors (Chart C) and shown not to revert. In addition, $\chi 1776$ has been tested for reversion following nitrosoguanidine and methyl methane sulfonate mutagenesis and no revertants were detected except Thy$^+$ revertants. Thus it is most likely that the Dap$^-$, Mal$^-$, Bio$^-$, Gal$^-$, Met$^-$, Thr$^-$ and Glyc$^-$ traits will not revert. The reversion of the thyA mutation was, however, quite unexpected, since it had been believed that the non-reverting thyA57 allele had been successfully transduced into $\chi 1776$.

Table 6 presents data on the frequency of alteration of several other phenotypic traits expressed by $\chi 1776$ and $\chi 1876$. The frequencies of deoB and deoC mutations that permit $\chi 1776$ and $\chi 1876$ to grow on media with 2 $\mu$g thymine/ml instead of with 40 $\mu$g/ml of either thymine or thymidine (Table 6) is about 1000 times higher than the frequency of such mutants that arise when selecting for Thy$^+$ revertants (see footnote to Table 5). As indicated later, these secondary mutations in $\chi 1776$ to deoB or deoC do not adversely affect the rates of thymineless death or survival during passage through the rat intestine. Revertants able to grow at 42° C. are also readily obtainable (Table 6), although they are not detected when high densities of cells ($>5\times10^7$) are plated. In comparing these revertants with thermoresistant transductants (see later), it was noted that some of the transductants plate at 100% efficiency at 42° C. compared to 37° C. whereas for three revertants tested, plating efficiencies at 42° C. were 0.3 to 0.7% of those at 37° C. The revertants also grow at 37° C. but not at 42° C. on supplemented MA whereas the TS$^r$ transductants grow on supplemented MA at both 37° and 42° C. TS$^r$ revertants and some transductants retain bile salts sensitivity and are unable to plate on MacConkey agar. It is thus likely that the revertants are due to various secondary mutational events that suppress the original mutant phenotype and are not due to reversion at the original mutational site. It is now believed that the TS phenotype is due to two mutations, oms-1 and oms-2, the latter of which is cotransducible with thyA, and both of which influence outer membrane structure, bile salts sensitivity, etc.

Revertants that can plate on media with either bile salts or detergents appear at similar frequencies (Table 6). Several colony types appear on MacConkey agar and on L agar+bile salts and these can be correlated with different levels of resistance to detergents. It is thus likely that several types of mutations are responsible for the bile salts- and detergent-resistance phenotypes. Those revertants that plate with high efficiency and form large colonies on both MacConkey agar and L agar containing bile salts (0.37% or more) have numerous associated changes that in some respects compromise the safety of $\chi 1776$ and $\chi 1876$. Of some interest is the observation that these high-level bile salts resistant revertants plate with low efficiency (about 1%) on L agar+DAP, Thd at 42° C. Even though this property is like the behavior of the TS$^r$ revertants, those TS$^r$ revertants so far tested retain bile salts sensitivity.

Verification of $\chi 1776$ genotype. The genotype of $\chi 1776$ was verified by using P1L4 transduction to select various transductant classes that could then be further tested. Table 7 presents the results of these transductions. Representative numbers of transductant colonies were picked into BSG+DAP, restreaked on the medium used to select them and then single colonies were picked and streaked on various selective media. All transductants selected as Thr$^+$, Mal$^+$, Thr$^+$ Mal$^+$ or Glyc$^+$ had the same properties and were Thr$^+$, Mal$^+$, Glyc$^+$, $\lambda^s$, T5$^r$, Bio$^-$, Met$^-$, Gal$^-$, Thy$^-$, Dap$^-$ and UV$^s$. These results along with the inability to obtain Bio$^+$ or Met$^+$ transductants implied the existence in $\chi 1776$ of two mutations giving the Met$^-$ phenotype (metC65 and $\Delta 29$[bioH-asd]) and two mutations giving the Bio$^-$ phenotype ($\Delta 40$[gal-uvrB] and $\Delta 29$[bioH-asd]). In corroboration, the Gal$^+$ transductants remained Thr$^-$, Met$^-$, Dap$^-$, Thy$^-$, Mal$^-$, Glyc$^-$ and Bio$^-$ but became UV$^r$ as expected and formed mucoid colonies under appropriate conditions which is indicative of ability to produce colanic acid. The Thy$^+$ transductants also had the expected properties and retained the phenotypes associated with all other mutations except that between 65 and 85% lost the thermosensitive property and some of these were shown to plate at 100% efficiency at 42° C. on both L agar and supplemented minimal agar. It is therefore evident that a mutation necessary for the TS phenotype is closely linked to thyA.

The so-called "Dap+ transductants" (Table 7) are an enigma since they are in fact Dap−. They remain Thr−, Mal−, Bio−, Glyc−, Met−, Thy−, Gal− and UV$^s$. When these transductants are grown in L broth containing DAP, Bio and Thd and plated directly on Penassay agar lacking DAP, some colonies will grow up provided that the Penassay agar contains NaCl. If these cultures are diluted 10 fold in BSG+DAP and then plated on Penassay agar lacking DAP, colonies will also appear if NaCl is included in the agar medium. $\chi$1776 cultures grown and plated in the same ways do not form colonies on DAP-deficient plates. If these transductant cultures are first diluted 1000 fold in BSG and then plated on Penassay agar with or without DAP, colonies are only formed on the medium containing DAP. These "DAP+ transductants" of $\chi$1776 form faster-growing colonies than $\chi$1776 on MA plates containing DAP, although after 3 days incubation at 37° C. the colonies are indistinguishable in size. "Dap+ transductants" may therefore represent phenotypes that require lower concentrations of DAP for growth and are thus able to derive sufficient amounts of DAP to sustain growth from the DAP contained in either the L broth+DAP growth medium or the BSG+DAP diluent that is added to the medium at the time of plating. It should be noted that these "Dap+" types grow slower than $\chi$1776 in broth media and have not been oberved to occur by mutation during reversion tests. In a further attempt to understand the nature of these "Dap+ transductants", they have been transduced to Thr+ to eliminate the Δ29[bioH-asd] mutation and were then shown to still possess the dapD8 mutation.

P1L4 was propagated on $\chi$1925, a bile salts resistant revertant of $\chi$1776 (Table 6) in order to further analyse some of the mutations in $\chi$1776. Various strains with galK and galT mutations were transduced to see if Gal+ transductants were formed. None were at frequencies that could have been up to $10^4$ times lower than the frequencies of Leu+ transductants selected in the same recipient. Thus the Δ40[gal-uvrB] mutation deletes most if not all, of the gal operon. P1L4 ($\chi$1925) was also used to transduce $\chi$1753 to LysA+ and a number of thyA cotransductants were selected to determine whether the thyA mutation did or did not revert when returned to a pure W1485 derived strain. Several of these thyA strains reverted to Thy+ at frequencies of about $10^{-9}$. P1L4 ($\chi$559) was also used to transduce $\chi$1753 to LysA+ thyA57 and several of these transductants failed to yield detectable ThyA+ revertants. It would thus appear that either the thyA allele in $\chi$1776 represents a new allele arising by mutation and not by transduction from $\chi$559 or the thyA57 mutation in $\chi$559 is really two separable mutations in the thyA gene with only one of them having been transduced into $\chi$1864 to yield $\chi$1776.

P1L4 transduction has also been used in an attempt to determine the genetic basis for the bile salts sensitivity trait that appeared concomitantly with the TS defect during transduction of $\chi$1849 to His+ with P1L4 ($\chi$289) to yield $\chi$1855 (Chart C). When P1L4 ($\chi$289) is used to transduce $\chi$1776 to ThyA+, 65 to 85% of the transductants become thermoresistant and regain partial but not complete resistance to bile salts. Gal+ transductants of $\chi$1776 obtained by using P1L4 ($\chi$289) retain bile salts sensitivity and fail to plate on MacConkey agar. These transductants also retain their temperature-sensitive phenotype but become UV resistant and regain the ability to synthesize colanic acid. It therefore appears that the Δ40[gal-uvrB] mutation is not necessary for expression of either bile salts sensitivity or temperature sensitivity. When $\chi$1849 is transduced to His+ with P1L4 grown on $\chi$289, $\chi$1038 or derivatives of the C600 and K-12-112 sublines, about 30% of the His+ transductants become bile salts sensitive and temperature sensitive. Since none of the His+ transductants of $\chi$1846 or any of its ancestors becomes bile salts sensitive, it is inferred that an additional mutation other than the Δ40[gal-uvrB] arose during the derivation of $\chi$1849 from $\chi$1846 which permits the expression of a mutation that is linked to his and is presumably present in many K-12 sublines. In accord with this idea is the fact that selection of bile salts resistant transductants of $\chi$1776 following transduction with P1L4 grown on $\chi$403, a his mutant derived from $\chi$289 (Table 1), results in a high yield of such transductants none of which become His−. These transductants, however, like the bile salts resistant revertants, are partially temperature resistant giving a $10^{-2}$ plating efficiency on L agar at 42° C. They also retain all of the other known mutational lesions of $\chi$1776 so this mutation designated oms-1 that permits the expression of the his-linked mutation in $\chi$1776 but which in the wild-type state prevents the expression of this his-linked mutation in various K-12 strains is not closely linked to any $\chi$1776 genetic marker. Based on cotransduction frequency data and phage sensitivity patterns it is believed that the his-linked mutation is in either the rfbA or rfbB locus. In another type of experiment in which an Hfr donor that transfers its chromosome clockwise commencing near the metC gene (minute 64) and which transfers the thyA-lysA region (minutes 60 to 61) last was mated with $\chi$1776, completely bile salts resistant transconjugants were formed early in the mating. These transconjugants were partially temperature resistant. All these results imply that the gene designated oms-1 that is present in $\chi$1849, is located in the 64 to 72 minute interval of the *E. coli* chromosome, and in conjunction with the rfb-2 allele confers sensitivity to bile salts, detergents, drugs, antibiotics, etc., resistance to phage and contributes to inability to grow at 42° C. These results also imply the existence of another gene oms-2 which first appeared in $\chi$1776, is located at about minute 60.2 on the *E. coli* chromosome linked to thyA and which augments the thermosensitivity and bile salts sensitivity of $\chi$1776. The inability of P1L4 transducing phage to propagate on $\chi$1776 makes a complete genetic analysis of the basis and interactions of the rfb-2, oms-1 and oms-2 mutations very difficult.

In testing for the restrictionless phenotype of $\chi$1776, it was first determined that phages 434, φ12, P1L4, 6SR, FP3, Br10, BF23 and φH were not restricted by the K-12 system. λ and 21 could not be tested on $\chi$1776, of course, because of the Δ29[bioH-asd] mutation nor could T1 and φ80 because of the tonA53 mutation. It was therefore decided to use the Thr+ transductants obtained from $\chi$1776 and λvir. The results obtained indicate that these $\chi$1776 Thr+ transductants are restrictionless. However, the $\chi$1776 Thr+ transductants gave a uniform 3-fold reduction in λvir plating efficiencies. It should also be noted that growth of host bacteria in L broth (which contains glucose) and plating on media lacking maltose results in a 90-fold reduction in plating efficiencies of λvir on the $\chi$1776 Thr+ transductants compared to plating on $\chi$289 for the same conditions. Growth of these host strains in a modified L broth medium containing maltose and plating on medium without maltose resulted in a 5-fold reduction. These effects are specific for the $_\chi$1776 derivatives since equal λvir plating efficiencies were obtained for all combinations of media with or without maltose for λvir plating on $_\chi$289 and $_\chi$1038. The restrictionless phenotype of $_\chi$1776 has also been confirmed by transformation with plasmid DNA from $_\chi$289 and $_\chi$1038 derivatives.

The presence of the supE42 mutation was also investigated using the $_\chi$1776 Thr+ transductants. λcI857 N7 N213 was found to give an efficiency of plating of about $10^{-1}$ on most of these strains when maltose was present in all media. When 0.1% glucose replaced 0.3% maltose in all media, no λcI857 N7 N213 plaques were observed. These results also show that the $_\chi$1776 Thr+ transductants are more dependent on maltose for λ growth but less able to support λ reproduction than are "wild-type" K-12 strains. The poor growth of the double N λ mutant, however, might imply that the supE42 allele in the $_\chi$1776 Thr+ transductants has been modified so as to only weakly suppress the double N λ mutant. To rule out this explanation, the pLM2 plasmid which has amber mutations in the bla and tet genes was introduced into $_\chi$1776. Resistance to both ampicillin and tetracycline were expressed normally thus indicating the presence of an unaltered supE42 allele.

Growth properties. The efficiencies of plating of $_\chi$1776 were tested on a variety of media in the presence and absence of cycloserine and nalidixic acid as a means to determine the best media for its growth and recovery from mixed populations of microorganisms and to verify certain expected phenotypes. (Similar, although more limited, tests were done with most of $_\chi$1776's ancestral parents and $_\chi$1876.)

$_\chi$1776 gives 100% plating efficiencies on appropriately supplemented L agar, Penassay agar and Minimal Agar containing glucose with or without Casamino acids. Plating efficiencies of 90 and 80 percent were observed on appropriately supplemented EMB and Brain Heart Infusion Agars, respectively. The plating efficiency on Minimal Agar containing Casamino acids with no added carbon source was $10^{-2}$ but was less than $10^{-6}$ when glycerol was added. This latter result is expected since the Δ29[bioH-asd] mutation deletes the gene for the aerobic glycerol phosphate dehydrogenase and thus glycerol phosphate should accumulate in cells and cause glycerol stasis. $_\chi$1776 also gives a $10^{-5}$ plating efficiency on Tryptone (1%) Agar containing DAP, Thd and Bio.

When high densities of $_\chi$1776 were plated on those media giving very low plating efficiencies, mutants and/or revertants were sometimes obtained. Such types were purified on the same selective media and then representative types were subjected to numerous tests. These tests included verification of relevant phenotypic properties (nutritional requirements; plating efficiencies; sensitivity to phages, antibiotics, detergents, etc.; rats of DAP-less and thymineless death; survival during passage through rats; etc.). All of these isolates had the same nutritional requirements as $_\chi$1776 and grew at the same or usually at slower rates than $_\chi$1776 in liquid media. With the exception of some of the bile salts resistant mutants, they possessed the same phenotypic traits and exhibited the same or faster rates of DAP-less and thymineless death as $_\chi$1776. Certain of these isolates did plate with altered efficiencies on certain media, especially on the medium on which selected.

Table 8 gives plating efficiencies for $_\chi$1776 on various media with different concentrations of nalidixic acid and/or cycloserine. EMB agar containing 75 μg nalidixic acid/ml was selected for recovery of strains from the mixed flora present in the rat intestine. It should be noted that yeast extract was omitted from EMB agar used to recover strains in rat feeding tests since it was desirable to make the medium as sparse as possible for the resident flora. Pdx and Ade were added to this medium since the former is required by $_\chi$1841 ($_\chi$1488 Nal$^r$) and the latter by many of $_\chi$1776's ancestors (see Chart C). Except in EMB agar, nalidixic acid was generally used at 25 μg/ml. Actually the minimal inhibitory concentration (MIC) of nalidixic acid for Nal$^s$ strains in EMB agar is double the MIC in L agar. Regular EMB agar (containing yeast extract, DAP and Thd) with 25 μg nalidixic acid/ml and sometimes with 10 to 15 μg cycloserine/ml is routinely used for transformation of $_\chi$1776 to preclude inadvertant and improbable transformation of a contaminant.

After doing a number of preliminary studies on the growth of $_\chi$1776 and $_\chi$1876 in complex liquid media it was decided that supplemented L broth gave better growth rates and cell yields than did either Penassay broth or Brain Heart Infusion broth. Thus $_\chi$1776 and $_\chi$1876 have generation times of 50 to 60 minutes in L broth+DAP+Thd, 85 to 95 minutes in ML+CAA+DAP+Bio+Thd+Glucose and 160 to 180 minutes in ML+Thr+Met+DAP+Bio+Thd+Glucose. $_\chi$1841 has generation times of about 42, 70 and 150 minutes in these three media. It is evident that the growth rates of $_\chi$1776 and $_\chi$1876 have decreased slightly over those exhibited by $_\chi$1841, the Nal$^r$ derivative of their ancestor $_\chi$1488. More recently more rapid rates of growth for $_\chi$1776 and $_\chi$1876 than indicated have been measured. Indeed, $_\chi$1776 can grow in supplemented ML with a generation time of 130 min. We believe that this more rapid growth is due to the greater awareness of the extreme sensitivity of $_\chi$1776 and $_\chi$1876 to ionic detergents and the consequent more meticulous care in washing and rinsing glassware. $_\chi$1776 and $_\chi$1876 seldom reach viable titers in excess of 5 to $8 \times 10^8$/ml. The reason for this is unknown but it is unlikely to be due to either exhaustion of nutrients or accumulation of toxic byproducts since when a culture at approximately $6 \times 10^8$ cells/ml is sedimented and then suspended in fresh medium no further increase in cell number is observed and the supernatant fluid from such a culture will permit regrowth of $_\chi$1776 cells to a titer of 5 to $8 \times 10^8$/ml.

Effect of temperature on survival and plasmid curing. When $_\chi$1776 is grown in L broth+DAP+Thd to log phase, suspended in BSG or L broth+DAP+Thd and then incubated at 43° C., exponential rates of loss in colony-forming ability are observed during the first 6 to 9 hours of incubation. Survival decreases 55% per hr in L broth and 84% per hr in BSG. It has also been observed that during 20 hours of growth in L broth or Penassay broth (+DAP and Thd) at 42° C., pSC101-containing derivatives of $_\chi$1846 and $_\chi$1849, but not of $_\chi$1841 ($_\chi$1488 Nal$^r$), lose pSC101 in 19 and 32 percent of the cells, respectively. This "curing" during incubation at 42° C. is therefore a property of the cells and not of the plasmid. Although $_\chi$1876 will not grow at 42° C., it will grow slowly at 41° C. and 3.4% of the cells growing overnight at this temperature lose pSC101. This property could be useful for certain experiments. pSC101 is completely stable in all four strains grown at 37° C., however, since loss of tetracycline resistance has not been observed in over 4000 clones tested by replica plating.

Resistance to bacteriophages. The responses of $\chi1776$, its ancestors and derivatives to various *E. coli* phages are presented in Table 10. These results were obtained by the cross streak method which can be somewhat insensitive for detecting either low levels of sensitivity or partial resistance. For example, phage 434 only gives a $10^{-3}$ efficiency of plating on $\chi1776$ compared to $\chi289$ although by the cross streak method it appears that $\chi1776$ is quite sensitive to 434. In terms of sensitivity to P1L4, variations in resistance during the derivation of $\chi1776$ from $\chi1488$ have been noted (Chart C). This was most apparent in terms of the large reduction in the efficiency of plating of P1L4 that accompanied the introduction of the his+ and bile salts sensitivity (presumably rfbA or rfbB; see later) markers in going from $\chi1849$ to $\chi1855$ and the gradual decrease in P1L4 ($\chi289$) transduction frequencies during the derivation of $\chi1776$ (Table 11). It should be noted that P1L4 efficiencies of plating of lower than $10^{-10}$ on $\chi1776$ were observed by use of both L media and P1 minimal media. A number of experiments have been conducted to evaluate the basis for the ability of P1L4 to transduce but not plaque on $\chi1776$. Using standard methodology along with anti-P1 serum, it has been observed that only 5% as much P1 infects $\chi1776$ as infects $\chi289$ during a 30 min adsorption period, that the latent period in $\chi1776$ is twice as long as in $\chi289$ and the mean burst sizes are the same in both strains. Additional evidence that the resistance of $\chi1776$ to P1L4 infection is due to defects in P1 infection and not in P1 propagation was obtained from studies on phage production following thermoinduction of P1cml clr100 lysogens of $\chi1776$ and $\chi289$. With both $\chi289$ and $\chi1776$ lysogens, the numbers of plaque-forming units and transducing phages specifying chloramphenicol resistance were the same.

It is worth noting that the bile salts resistant revertants of $\chi1776$ and $\chi1876$ ($\chi1925$ and $\chi1928$) regain sensitivity to phages P1L4, D108, $\phi$W, PV, Br60 and C21 and resistance to $\phi12$ as displayed by $\chi1849$ (Table 10). It is therefore evident that the change in the bacterial cell surface associated with bile salts sensitivity also affects the ability of numerous phages to interact with that cell surface.

Taken collectively, these studies on resistance of $\chi1776$ to various phages indicate that $\chi1776$ is completely resistant to the specialized transducing phages $\lambda$, 21 and $\phi80$, is probably completely resistant to Mu, D108 and T1 which are capable of low frequencies of generalized transduction, is partially resistant to the specialized transducing phage 434 and is partially resistant to the generalized transducing phage P1. Although these changes are likely to reduce the probability of potential transductional gene transfer from $\chi1776$ in nature, it is also evident that the cell surface changes in $\chi1776$ now endow it with sensitivity to some known phages (Table 10) and probably to unknown phages which may be capable of specialized or generalized transduction.

Response to antibiotics, mutagens, drugs, detergents and bile salts. Table 12 lists the minimal inhibitory concentration (MIC) of numerous antibiotics, mutagens, drugs, detergents and bile salts for $\chi289$, $\chi1841$ ($\chi1488$ Nal$^r$), $\chi1776$ and $\chi1876$ and one bile salts resistant derivative of $\chi1776$ ($\chi1925$; see Table 6. These data indicate that $\chi1776$ and $\chi1876$ are more sensitive to almost all tested compounds than their ancestors. Exceptions to this general rule are the increased resistance to nalidixic acid (due to nalA25 mutation), trimethoprim (due to thyA57* mutation) and cycloserine (due to cycA1 and cycB2 mutations) and for $\chi1876$ to tetracycline (due to the pSC101 plasmid). In this last regard, it should be noted that $\chi1876$'s MIC for tetracycline (50 $\mu$g/ml) is lower than the MIC for tetracycline needed for other "normal" strains harboring pSC101 (100 to 200 $\mu$g/ml). Indeed, $\chi1876$ does not plate with 100% efficiency on agar medium containing more than 12.5 $\mu$g tetracycline/ml whereas $\chi1841$ and $\chi1846$ derivatives containing pSC101 will plate with 100% efficiencies on agar medium containing 50 or even 100 $\mu$g tetracycline/ml. It is thus likely that the introduction into $\chi1776$ of plasmid cloning vectors that specify resistance to other antibiotics will result in strains that express lower levels of antibiotic resistance than would "normal" strains of *E. coli* K-12.

The increased sensitivities of $\chi1776$ and $\chi1876$ to chloramphenicol should reduce the quantities of this drug needed to cause amplification of ColE1-derived plasmid cloning vectors. The extreme sensitivity of these strains to rifampicin should also be useful in studies on chimeric plasmid directed RNA synthesis in minicells.

The bile salts resistance derivative $\chi1925$ regains complete resistance to sodium dodecyl sulfate, sarkosyl, deoxycholate, bile salts and rifampin, partial resistance to streptomycin, spectinomycin and kanamycin and is unchanged with regard to its increased sensitivity to chloramphenicol, tetracycline and mitomycin C when compared to the responses of $\chi289$, $\chi1841$ and $\chi1776$ (Table 12). It is thus likely that the mutations conferring senstivity to bile salts are also responsible for the increased sensitivity of $\chi1776$ to most, if not all, of these other compounds.

In kinetic experiments, $\chi1776$ is rapidly killed by either 0.15% bile salts or 0.02% sodium dodecyl sulfate whereas $\chi289$ grows well in the combined presence of 0.15% bile salts and 0.4% sodium dodecyl sulfate. In other experiments, it has been found that $\chi289$ grows normally in L broth containing either 0.75% bile salts or 1% sodium dodecyl sulfate. $\chi1876$ shows the same rates of killings by bile salts and sodium dodecyl sulfate as found for $\chi1776$. Increasing the bile salts concentration above 0.15% does not accelerate the rates of killings of $\chi1776$ and $\chi1876$ whereas use of sodium dodecyl sulfate at 0.1% or above gives the maximum rate of killing observed for bile salts. The extreme sensitivity of $\chi1776$ to detergents should facilitate its use for plasmid DNA isolation and the sensitivity to bile salts should reduce its survival in the intestinal tract of animals. The extreme sensitivity of $\chi1776$ to ionic detergents can, however, complicate transformation experiments in which the DNA is obtained from cells by ionic detergent facilitated lysis. It is therefore very important to either carefully dialyze the DNA to remove traces of ionic detergent or use non-ionic detergents for DNA isolation since $CaCl_2$-treated, cold-incubated, heat-shocked $\chi1776$ cells are rapidly killed by very low concentrations of ionic detergents.

Basis for assignment of one mutation conferring bile salts sensitivity to rfbA or rfbB locus. In *E. coli* K-12, the structure of the LPS has recently been characterized as [lipid A, $(P_i)_n$, ketodeoxyoctanate]-[heptose]-[(glucose)$_4$]-[(glucose)$_2$-(galactose)$_2$-rhamnose]. The removal of galactose, and consequently the rhamnose, which is due to galE or galU mutations, permits sensitivity to phage C21 which can infect $\chi1849$ and the bile salts resistant derivatives, $\chi$1925 and $\chi$1928, but not $\chi$1776 and $\chi$1876 (Table 10). Phage C21 infection requires the heptose-(glucose)$_4$ structure but is independent of the terminal two glucose moieties that are added in the form of UDP-glucose whose synthesis is regulated by the galU gene. Furthermore, since the Gal+ transductants of $\chi$1776 (Table 7) can produce colanic acid, the bile salts sensitivity mutation in $\chi$1776 cannot block colanic acid synthesis and cannot therefore be in galU. The four glucose moieties attached to heptose in the LPS are added as TDP-glucose whose synthesis is controlled by the rfbA and rfbB loci. A mutation in either gene would therefore confer resistance to C21. Mutations in the lpcA, lpcB and rfa genes affect the $(P_i)_n$ and heptose in the LPS core, confer increased sensitivity to antibiotics and resistance to phage T4. These mutations also confer resistance to P1 and to bile salts, detergents, etc. Since $\chi$1776 remains sensitive to T4, T7 and to some of the other rough-specific phages (FP3, BR10, 5SR) and is only partially resistant to P1, mutations in lpcA, lpcB and rfa genes can reasonably be excluded as being responsible for $\chi$1776's phenotype. Mutations in envA and envB can also be excluded since they are associated with anomolous cell division and unusual cell shapes that are not characteristic of $\chi$1776. It is therefore inferred that it is most likely that one of the mutations conferring bile salts sensitivity, which first appeared in $\chi$1855, is located in either the rfbA or rfbB gene which would be about 30% cotransducible with the his operon. It should be recalled that the data presented strongly suggest that this supposed rfb allele is present but not expressed in $\chi$289 and other K-12 sublines and that its expression in $\chi$1855 is due to the presence of another mutation designated oms-1 which arose in $\chi$1849.

Sensitivity to UV and fluorescent light. In that the $\Delta$40[gal-uvrB] mutation deletes one of the genes specifying the endonuclease needed to make incisions in DNA adjacent to pyrimidine dimers (uvrB) and the gene for the photoreactivating enzyme (phr), it would be expected that $\chi$1776 and $\chi$1876 would be extremely sensitive to UV irradiation and would be unable to repair UV-induced dimers when illuminated with 365 nm light. These predictions have been experimentally confirmed by measurement of survival as a function of UV exposure dose and by illumination of cells with black light fluorescent light. The sensitivity of $\chi$1846 and $\chi$1776 to fluorescent light has also been measured to determine whether work with $\chi$1776 should be conducted in laboratories with either subdued or yellow lights. Cells were suspended in BSG+DAP+Thd and illuminated at room temperature in closed wettable plastic tissue culture dishes with two parallel 15 watt cool white fluorescent tubes (Sylvania F15T-CW) held in a standard desk lamp 10 cm above the cultures. After 48 hr, $\chi$1846 had a survival of 6% and $\chi$1776 of 0.07%. The increased sensitivity of $\chi$1776 compared to $\chi$1846 is most likely accounted for the small amounts of UV wavelengths that pass through the glass of the fluorescent tubes and the plastic lids of the cell culture dishes that contain the cells and also to the fact that $\chi$1776 dies somewhat more rapidly than "wild-type" strains when starved in BSG at room temperature.

SURVIVAL OF STRAINS

Dap-less death. The rates of DAP-less death for $\chi$1776 and $\chi$1876 have been examined many times under numerous conditions. Dap-less death occurs at reasonable rates when conditions are favorable for the cells to carry out macromolecular synthesis as occurs in L broth+Thd and in ML+Casamino acids+Bio, Thd, Glc. However, in supplemented ML lacking both DAP and lysine there is little or no DAP-less death with the loss of colony forming units being similar to what is observed for suspension of $\chi$1776 in BSG. When lysine is added to ML, protein synthesis becomes possible and DAP-less death ensues but at slower rates than observed in the richer media. DAP-less death in all cases was accompanied by defective cell wall biosynthesis as visualized in the light microscope and by lysis as revealed by optical density measurements.

In some of the early experiments on DAP-less death, the effects of the addition of nalidixic acid and/or cycloserine at various concentrations to the liquid media as well as to various plating media were investigated. Based on all these and other studies it is recommended that nalidixic acid be used at no more than 25 $\mu$g/ml in L broth and L agar when monitoring the survival of $\chi$1776 and $\chi$1876, although up to 75 $\mu$g/ml can be tolerated in EMB agar. Cycloserine can also be added to these media at concentrations up to 10 $\mu$g/ml with maximum recovery of viable cells.

During the genetic construction of $\chi$1776 and prior to the introduction of the $\Delta$40[gal-uvrB] mutation to block colanic acid biosynthesis, it was observed that the rate of DAP-less death was dependent on the NaCl concentration in L broth. It was experimentally determined that the presence of NaCl in L broth markedly decreases the rate of DAP-less death for $\chi$1846 (which is able to produce colanic acid), but has less effect on the behavior of $\chi$1849 and displays no effect on the survival rate of $\chi$1776. In numerous experiments with $\chi$1776 and $\chi$1876 using both exponentially-growing and stationary-phase inocula and in which the initial density was varied from $10^6$ to $10^{10}$ cells/ml, no significant differences in the initial rates of DAP-less death dependent on the presence or absence of NaCl in the medium have been observed. Since NaCl does confer a slight but reproducible protective effect on $\chi$1849, one or more of the genetic changes in going from $\chi$1849 to $\chi$1776 (Chart C) has abolished this effect of NaCl in diminishing the rate of DAP-less death. It has been found, however, that the ability of $\chi$1776 and $\chi$1876 cells which survive 6 to 10 hours of DAP starvation to grow slowly during the next 60 to 90 hours in L broth lacking DAP seems to be dependent on (or at least facilitated by) the presence of NaCl in the L broth. In other words, in L broth lacking NaCl $\chi$1776 and $\chi$1876 cells die completely whereas in the regular L broth which contains NaCl the slow regrowth of surviving cells is sometimes observed. It would thus seem logical to suspect that NaCl may facilitate the scavenging of DAP released by lysing cells. In this regard, it should be recalled that the "Dap+ transductants" (Table 7) are also unable to form colonies on L agar lacking both DAP and NaCl even when plated from the BSG+DAP diluent. Since $Mg^{++}$, $Ca^{++}$ and $K^+$ can substitute for $Na^+$ in stimulating colanic acid synthesis and in permitting long-term survival of Dap$^-$ strains (Pereira and Curtiss, unpublished), it is likely that $\chi$1776 and $\chi$1876 would survive less well in natural environments with low concentrations of cations.

The rates of DAP-less death have also been measured for inocula of different densities using log-phase and stationary-phase cultures, respectively. The fact that cells from log-phase cultures die more rapidly and to a greater extent than cells from stationary-phase cultures supports the conclusion that the rate and extent of DAP-less death increases as the metabolic growth potential of the cells increases. This conclusion is also supported by the observation that DAP-less death is very inefficient when very high cell densities are inoculated into the L broth lacking DAP.

In a number of experiments, it was observed that $\chi 1776$ and $\chi 1876$ whether under permissive or non-permissive conditions were adversely affected by the presence of more robust bacterial strains including a great diversity of laboratory contaminants such as strains of Pseudomonas, Staphylococcus and Serratia. The conclusion from these observations as well as from reconstruction experiments is that $\chi 1776$ and $\chi 1876$ are poorly able to compete with other "wild-type" microorganisms and thus are less able to survive and indeed die at faster rates in the presence of other microorganisms than in their absence. This finding should make it even less likely that $\chi 1776$ could survive in nature should it inadvertantly escape its carefully defined "laboratory" environment.

Since $\chi 1776$ and $\chi 1876$ are sensitive to bile salts and ionic detergents, their effects on DAP-less death were checked. Differences, although slight, were noted with sodium dodecyl sulfate increasing slightly and bile salts decreasing slightly the rates of DAP-less death. It has also been noted that the addition of ampicillin (100 $\mu$g/ml) and/or cycloserine (100 $\mu$g/ml) to $\chi 1776$ cultures in DAP-deficient media accelerates the rates of death over that observed with DAP starvation alone.

This observation has therefore contributed to the development of an efficient method combining DAP-less and thymineless death with the addition of cycloserine and ampicillin as a very efficient means to enrich for mutant derivatives of $\chi 1776$ as described hereinafter.

The rates of DAP-less death for three bile salts resistant derivatives from $\chi 1776$ have been measured. $\chi 1925$ (Table 6) and $\chi 1951$ appear to be complete revertants to bile salts resistance in that they have properties similar to those of $\chi 1849$. $\chi 1926$, on the other hand, is only a partial revertant since it does not plate with high efficiency on L agar+0.15% bile salts (Table 6). The rates and extents of DAP-less death of these bile salts resistant revertants were similar to those found for $\chi 1776$ and $\chi 1876$ although substantially decreased rates of DAP-less death have been noted on one or two occasions.

Thymineless death. $\chi 1776$ and $\chi 1876$ do not undergo thymineless death in L broth (as expected since they grow well in L broth without Thy or Thd) but did in ML and in ML containing Casamino acids. In both of these synthetic media, when cells surviving 20 hours starvation were grown under permissive conditions and then retested for thymineless death, the same rates of thymineless death were observed. It was also observed that prolonged starvation leads to slow regrowth of cells and a high percentage of the cells present at 72 or 96 hours have deoB or deoC mutations since they grow well on supplemented MA with 2 $\mu$g thymine/ml. Thymineless death does not occur when very high cell densities are used and density rather than growth phase of the culture at the inception of starvation is the more important factor in governing the rate and extent of thymineless death. Rate of growth is also important since thymineless death is usually more extensive in ML containing Casamino acids than in ML without Casamino acids.

Combined DAP-less and thymineless death. The combined effects of starvation for both DAP and thymidine in L broth, ML+CAA, Bio, Glc and ML+Thr, Met, Lys, Bio, Glc for $\chi 1776$ and $\chi 1876$ have been measured. Both the rates and final levels of survival were similar to those obtained for DAP or thymine starvation alone in the respective media. Thus the two types of starvation do not act synergistically. However, slow regrowth of cultures was never observed to occur in either ML medium even when incubations were continued for more than 100 hours.

DNA degradation during DAP-less and/or thymineless death. Since thymineless death results in single-strand breaks in DNA and should thus lead to DNA degradation, the rates of solubilization of [$^3$H]thymidine labeled DNA in $\chi 1776$ and $\chi 1876$ undergoing DAP-less and/or thymineless death was examined. More DNA is solubilized during DAP-less death (with or without simultaneous starvation for thymidine) than during thymineless death. This is presumably due to the liberation of both DNA and nucleases during DAP-less death with the consequence that the liberated DNA is rapidly degraded in the culture medium.

Prelabeled $\chi 1776$ and $\chi 1876$ DNA were analysed on alkaline sucrose gradients during thymineless death in ML+Casamino acids, DAP, Bio, Glc medium. There was no appreciable decrease in single-strand molecular weights accompanying the decrease in total acid-insoluble material and it thus appears that DNA degradation in $\chi 1776$ and $\chi 1876$ is an all or none response for each cell.

Survival in non-growth media. The survivals of $\chi 1776$ and $\chi 1876$ were measured under a variety of conditions that would not permit growth. The survival data for $\chi 289$, $\chi 1776$ and $\chi 1876$ in BSG, tap water and deionized water at room temperature were measured. Although death is slow in these media, as it is in ML lacking DAP and lysine, the $\chi 1776$ and $\chi 1876$ cells surviving after 8 days exhibited a two-fold greater sensitivity to sodium dodecyl sulfate, sarkosyl and bile salts than the original $\chi 1776$ and $\chi 1876$ cultures. On the other hand, the sensitivity of $\chi 289$ to these compounds did not change during the starvation time. It has also been observed that aeration of $\chi 1776$ and $\chi 1876$ cells suspended in water, but not in BSG, accelerates their rates of death compared to $\chi 289$.

When $\chi 1776$ and $\chi 1876$ were suspended in BSG or L broth+DAP+Thd and stored at 4° C., there was no detectable loss in viability over a period of two weeks. $\chi 1776$ and $\chi 1876$ cells were also suspended in 1% peptone-5% glycerol (containing DAP and thymidine) and two ml amounts placed in screw cap Wasserman tubes to determine the effects of rapid freezing and thawing. Freezing of $\chi 1776$ and $\chi 1876$ resulted in about a 50% loss in viability per freeze-thaw cycle whereas $\chi 289$ exhibited a 30% loss in viability per cycle. There thus appears to be no difficulty in keeping $\chi 1776$ and $\chi 1876$ under non-physiological conditions that are customary for short-term and long-term storage of viable bacterial cultures.

Survival during passage through rats. During construction of $\chi 1776$, the ability of various strains to survive and/or multiply during passage through the intestinal tract of rats has been tested repeatedly to determine which mutations were or were not important in precluding such survival. High concentrations of cells have been fed by using a stomach tube so that measured quantities of cells could be delivered down the esophagus. Cells were always suspended in milk so as to circumvent, as much as possible, problems associated with the acidity of the stomach. In general, weanling rats have been used although older rats have also been tested. The results of some of these tests are summarized in Table 13.

The prototroph $\chi$1833 ($\chi$289 Nal$^r$) survives this passage rather well and indeed must multiply to some extent to explain the excretion of between $10^6$ and $10^8$ cells per 0.1 g feces during the first day or two after feeding and the continued excretion for several days. $\chi$1922 which is a thyA derivative of $\chi$1833 survives slightly less well than $\chi$1833 which indicates that the thyA mutation must provide some selective disadvantage during passage through the intestinal tract. This point has been verified in tests with other thyA strains. $\chi$1841, which is the Nal$^r$ derivative of $\chi$1488 [the first strain derived from $\chi$1276 during the construction of $\chi$1776 (see Chart C)], has about the same survival characteristics as $\chi$1922. The double Dap$^-$ strain $\chi$1846, which can still synthesize colanic acid, survives a little less well and $\chi$1849, which was isolated from $\chi$1846 and cannot produce colanic acid, is killed off even more rapidly. All these strains, however, do survive passage through the intestinal tract. It is therefore evident that the six hours that it takes a fed strain to appear in feces is an insufficient length of time to permit enough metabolism for 100% DAP-less death to occur.

The various bile salts sensitive derivatives of $\chi$1849, however, have never been observed to survive passage through the intestinal tract under normal conditions (Table 13). A further indication of the importance of the bile salts sensitivity trait is the ability of $\chi$1925 and $\chi$1928 (two bile salts resistant revertants of $\chi$1776 and $\chi$1876, respectively) to survive passage through the intestinal tract. Neither of these strains survives as well as $\chi$1849, however, but this may be explainable if $\chi$1925 and $\chi$1928 do not represent true revertants for the bile salts sensitivity trait. Indeed, the bile salts resistant derivative $\chi$1926, which is still partially bile salts sensitive (Table 6) and is therefore probably not a true revertant, does not survive passage through the rat's intestinal tract. Five different $\chi$1776 derivatives that were selected for their ability to grow or form larger colonies on various medial were also unable to survive passage through the rat's intestine. A TS$^r$ revertant of $\chi$1776 ($\chi$1929) fared no better. A deoC derivative of $\chi$1776 ($\chi$1930) that can grow with low levels of thymine also cannot survive passage through the rat's intestine. In this regard, it is known from studies with other strains that the deoC mutation decreases intestinal survival of thyA strains although the deoB mutation has no effect.

Of some interest is the observation that the feeding of tetracycline to the rats for one day prior to and during feeding of $\chi$1876 results in survival of some $\chi$1876 cells. The dose of tetracycline given was rather high so it might be that DAP-less and/or thymineless death was inhibited due to tetracycline-induced growth inhibition, in which case the lower survival of $\chi$1876 was probably due to bile salts sensitivity. This explanation is partially validated by the observation that the $\chi$1876 bile salts resistant derivative, $\chi$1928, gave higher surviving titers in feces following tetracycline feeding than did $\chi$1876. These results, however, emphasize the need to follow the dictum that individuals working with recombinant DNA molecules should not engage in such work during and for seven days after cessation of antibiotic therapy.

POTENTIAL FOR TRANSMISSIBILITY OF GENETIC INFORMATION BY STRAINS

Conjugational recipient ability under permissive conditions. Since conjugational transmission of chimeric plasmids may well be the most likely means for successful escape and perpetuation of cloned DNA, over five hundred matings were performed with $\chi$1776, its derivatives and its ancestors to assess recipient and donor ability under a diversity of conditions; 22 different conjugative plasmids that represent 15 different incompatibility groups were employed for these studies.

In terms of recipient ability, $\chi$1841, $\chi$1849 and $\chi$1776 were mated with 22 donors, each with a different conjugative plasmid and which collectively represent 15 incompatibility groups. These matings have been performed under optimal permissive conditions to assess the contributions of different mutations in $\chi$1776 to diminish its recipient ability. Since plasmids in certain incompatibility groups are prevalent in microorganisms that inhabit soil, water, the intestinal tracts of fish, etc., these matings were carried out at 27°, 32° and 37° C. to assess the contribution of temperature to the efficiency of plasmid transfer. Most of these matings were conducted for 24 hours with transconjugant yields and parental titers being determined after 30 and 90 minutes and 24 hours of mating. It became readily apparent, however, that the viable $\chi$1776 titer dropped 10 to 10,000 fold after 24 hours of mating at 37° C. and since this would also account for the observed decrease in transconjugant titers, 24 hour matings were discontinued to evaluate $\chi$1776's recipient ability. This behavior was noted in matings with 11 different donors (the other 11 were not examined for this property). Of interest is the fact that $\chi$1776 remains viable and indeed grows at 32° C. in the presence of other bacteria provided that DAP is present.

Recipient ability of $\chi$1776 has been tested with donors harboring conjugative plasmids in the C, FI, FII, H, I$\alpha$, J, L, M, N, O, P, T, W, X, 9, and 10 incompatibility groups. For matings under optimal permissive conditions at 37° C., the frequency of transfer was $10^{-1}$ for one I-type plasmid (R64-11), $10^{-2}$ for various FII plasmids, $10^{-3}$ to $10^{-4}$ for the N and other I$\alpha$ plasmids, $10^{-5}$ for P plasmids, $10^{-6}$ for Inc 9 plasmids, $10^{-7}$ for L, M, and Inc 10 plasmids, $10^{-8}$ for T plasmids, and less than $10^{-9}$ for C, H, and X plasmids.

Generally, matings conducted at the lower temperature of 32° C. resulted in a decreased transconjugant frequency. There were, however, three exceptions to this behavior: R27 (H), R831 (L), and R394 (T) were able to transfer 1000-fold, 10-fold, and 100,000-fold better, respectively, at 32° C. The recipient ability of $\chi$1776 for R831 and R394 decreased about 10-fold when the mating temperature was further reduced to 27° C., but for R27 there was another 10-fold increase in transconjugant frequency at the lower temperature. When the mating temperature was 22° C., the transconjugant frequency was about the same as when matings with the donor possessing R27 had been conducted at 32° C.

The lower temperature of 27° C. also appears to increase the transconjugant frequency in matings between $\chi$1776 and donors possessing C or M type plasmids, although the frequencies are quite low: $10^{-7}$ and $10^{-6}$, respectively. With all other plasmids, except the ones mentioned above, transconjugant frequencies from matings conducted at 27° C. were decreased in comparison to those obtained in matings at 37° C. or 32° C. and were, in fact, quite low: $10^{-6}$ to less than $10^{-9}$.

The ability of $_\chi$1776 to receive plasmids from the various donors under optimal permissive mating conditions, when compared to the recipient ability of $_\chi$1841, shows the following pattern:

1. the transconjugant frequency for $_\chi$1776 is less than 10-fold lower than that for $_\chi$1841. This behavior was demonstrated by one FII and three I-type plasmids and plasmids of the H, N, P, W, and 9 incompatibility groups. For most of these plasmids, the recipient ability of $_\chi$1776 was 2- to 6-fold lower than that of $_\chi$1841, but $_\chi$1776 was actually able to receive RP4, a P-type plasmid, at about twice the frequency at which $_\chi$1841 received the same plasmid.

2. the transconjugant frequency for $_\chi$1776 was 10- to 100-fold lower than that for $_\chi$1841. Included in this group were the other FII and one I-type plasmid, C, and M-type plasmids.

3. the transconjugant frequency for $_\chi$1776 was 1000- to 100,000-fold lower than that for $_\chi$1841. Plasmids of the J, L, O, T, X, and 10 incompatibility groups exhibited this type of behavior.

In other matings with $_\chi$1849, which possesses the Δ40[gal-uvrB] mutation, it has been possible to show a significant reduction in transconjugant frequency compared to the recipient ability of $_\chi$1841 for conjugative plasmids in the C, J, L, M, O, T, X, and 10 incompatibility groups. Thus the Δ40[gal-uvrB] mutation contributes to the Con$^-$ phenotype of $_\chi$1776. By using $_\chi$1925, a bile salts resistant revertant of $_\chi$1776, it has also been possible to show that the decreased recipient ability of $_\chi$1776 for certain conjugative plasmids is due to the combined effects of the rfb-2, oms-1 and oms-2 mutations.

In terms of evaluating the ability of $_\chi$1776 to acquire a conjugative plasmid which would be necessary for the mobilization and transmission of a non-conjugative plasmid vector, several factors should be considered. First, it should be mentioned that Rldrd19, R100drd1, R64drd11 and R549drd1 are derepressed for expression of the donor phenotype such that donors that possess them are (or should be) 100- to 10,000 times more fertile than donors possessing wild-type repressed conjugative plasmids. Indeed, only three derepressed conjugative plasmids have ever been isolated in nature; namely, F (which might have actually mutated during its 40 years sojourn in *E. coli* K-12), ColV and one R plasmid. These derepressed plasmids were therefore used only to maximize the ability to detect rare events. However, it should be noted that donors harboring R648 (IncIα) and R66a-1 (IncIα) give transconjugant yields in matings with $_\chi$1841 that are approaching those expected for transfer of derepressed plasmids. Second, the yield of transconjugants inheriting IncIα and IncFII plasmids decreases as the square of the dilution in the bacterial mating density below $10^8$ cells/ml. Thus, transconjugant yields are decreased about 10,000-fold for matings of one hour duration conducted at cell densities of $10^6$/ml which is the approximate density of *E. coli* found in the mammalian intestinal tract. Third, there exist other barriers to acquisition of conjugative plasmids in nature which include the frequency of potential donors possessing conjugative plasmids (about 10 percent), the presence of restriction-modification systems in most microorganisms and the existence of entry exclusion, incompatibility and donor cell surface properties. All of these factors greatly diminish the likelihood that $_\chi$1776 containing a non-conjugative plasmid could acquire such a conjugative plasmid in nature. The low survival potential of $_\chi$1776 in natural environments would also make it highly unlikely that $_\chi$1776 could ever survive long enough to transmit recombinant DNA to other organisms even if it did acquire such a conjugative plasmid.

Mobilization of pSC101 by conjugative plasmids under permissive conditions. In order to evaluate the consequences of the acquisition of a conjugative plasmid by $_\chi$1776 on the subsequent potential to transmit DNA cloned on the pSC101 non-conjugative plasmid vector, derivatives of $_\chi$1876 were constructed that possessed various conjugative R plasmids that did not express tetracycline resistance. All these R plasmids were stable in $_\chi$1876 and did not cause $_\chi$1876 to lose pSC101 during cultivation at 37° C. These donors were then mated with $_\chi$1763 and the titers of both parents and all transconjugant classes measured after 1, 6 and 24 hours at 37° C. In addition to providing data on the mobilization of pSC101, these matings also evaluated the potential of $_\chi$1876 (and thus $_\chi$1776) to act as donors of the various conjugative plasmids. It was found that $_\chi$1876 exhibits normal donor ability during 60 minutes of mating for the transfer of Rldrd19, R549drd1, R69/2, R66a-1 and R648 and is defective in the transfer of R394 and R40a when compared to the donor ability of $_\chi$1753 derivatives harboring these plasmids. It should be noted, however, that the recipient ability of $_\chi$1776 for the IncT plasmid R394 is almost 5,000 times higher in matings at 27° C. than in matings at 37° C. and it is thus conceivable that the donor ability of a $_\chi$1876 derivative harboring R394 might also increase with a decrease in mating temperature. In any event, it is evident that the IncM plasmid R69/2 mobilizes pSC101 as efficiently as itself and compared to their own transfer frequencies that the IncIα plasmids R549drd1 and R648 mobilizes pSC101 at a $10^{-1}$ to $10^{-2}$ frequency, that the IncIα plasmid R66a-1 mobilize pSC101 at a $10^{-2}$ to $10^{-3}$ frequency and that the IncFII plasmid Rldrd19 mobilizes pSC101 at a $10^{-3}$ to $10^{-4}$ frequency. The R40a (IncC) and R394 (IncT) plasmids did not give detectable frequencies of pSC101 mobilization. $_\chi$1876 donors generally decreased in titer during the 24 hours of mating. It should be noted, however, that although the total $_\chi$1763 titer increased about 10-fold between 6 and 24 hours of mating, the $_\chi$1763 derivatives inheriting pSC101 (with or without the conjugative R plasmid) did not increase at all and even decreased during this same interval. Since the transconjugants selected for inheriting the conjugative plasmid alone did increase in titer during this interval, it is inferred that many of the stationary phase $_\chi$1763 cells that possessed pSC101 could not plate on medium with 12.5 μg tetracycline/ml. This inference is based on the fact that expression of the tetracycline resistance specified by pSC101 is inducible and not constitutive and the fact that stationary phase cells, when placed in conditions for growth, are poorly equipped to immediately begin synthesis of a protein needed for their survival.

Triparental matings under permissive conditions. As another means to assess the likelihood that $_\chi$1776 possessing a chimeric plasmid could transmit the cloned DNA to some other microorganism, triparental matings were performed using a series of $_\chi$1753 derived primary donors in matings with $_\chi$1876 and the secondary recipient $_\chi$1763. In these matings, conducted under optimal permissive conditions at 37° C., pSC101 was transferred to $\chi$1763 in the presence of primary donors possessing the derepressed I$\alpha$ plasmid R549drd1 ($10^5$/ml), the I$\alpha$ plasmids R648 and R66a-1 and the L plasmid R471a ($10^3$/ml), the derepressed FI plasmid F'his+ and the M plasmid R69/2 ($10^2$/ml), and the derepressed FII plasmid Rldrd19 and the T plasmid R394 ($10^1$/ml). No pSC101 transmission was detected in matings with primary donors possessing one C and one Inc10 group plasmid. Of interest is the observation that triparental matings with the donors possessing the R394 plasmid yielded very low frequencies of pSC101 transconjugants in $\chi$1763, whereas $\chi$1876 derivatives harboring R394 did not yield pSC101 transconjugants in matings with $\chi$1763 (except for a few colonies after 24 hours of mating with the R40a+ donor). The decline in $\chi$1876 titer during the course of mating in some but not all matings was also apparent from the data obtained.

Conjugational ability during DAP-less and/or thymineless death. Studies on the recipient and donor ability of $\chi$1776 and $\chi$1876 under non-permissive conditions were restricted to studies using the derepressed IncFII plasmid Rldrd19. A $\chi$1776 derivative possessing Rldrd19 loses the ability to transfer Rldrd19 to $\chi$1763 at a rate that is proportional to the rate of donor cell death. Indeed, surviving Rldrd19 $\chi$1776 cells are almost as efficient on a per cell basis as non-starving Rldrd19 $\chi$1776 cells in conjugational plasmid transfer. This is also true for starvation in ML medium with or without Casamino acids where starvation for thymine might be expected to block conjugational plasmid transfer even by surviving cells. Obviously, either these surviving cells have a sufficient pool of thymine-containing nucleotides to support conjugational plasmid replication or conjugational plasmid transfer does not depend on concomitant conjugational DNA replication.

Conjugational ability as a function of starvation time in non-growth liquid media. The ability of $\chi$1776 to receive Rldrd19 from $\chi$1792 was measured as a function of starvation and mating time in water, BSG and ML+glucose at 24° C. and 37° C. Transconjugants were essentially undetectable for matings in water and BSG at both temperatures and were diminished 10,000 to 100 fold for matings in ML+ glucose at 24° C. and 37° C., respectively, compared to yields observed in L broth matings under permissive conditions. When $\chi$1792 and $\chi$1776 were starved for 4 hours in these non-growth media, transconjugants were either absent or decreased another 10 to 100 fold over what was observed without starvation. In general, recipient ability is retained better during starvation in ML+glucose than in BSG and at 37° C. than at 24° C. It should be noted that these measures of $\chi$1776's recipient ability cannot be due to plate matings, since nalidixic acid was included in the selective medium and immediately causes plasmid transfer to cease. It is interesting to note that although growth of cells possessing IncF group plasmids at 28° C. or less yields phenocopies unable to mate, starvation at 24° C. of donor cells that were originally grown at 37° C. does not abolish $\chi$1792's donor fertility. It is known that starvation of donor cultures at 37° C. also leads to loss of donor fertility although starvation as a standing culture without vigorous aeration causes the lowest rate of loss in donor ability and this may account for the low yield of transconjugants formed at 37° C.

The donor ability of $\chi$1776 containing the Rldrd19 plasmid was also measured with and without starvation in water, BSG and ML+glucose at 23°, 37° and 43° C. No plasmid transfer to $\chi$1763 was observed for any matings at 43° C. nor for matings in water or BSG at 23° C. Donor ability was decreased 100 to $10^7$ fold for all other conditions with water being the poorest mating condition.

These studies indicate that most of the non-permissive conditions likely to be encountered in nature will not be conducive to conjugational transmission of plasmid chimeras.

Potential for transductional transmission under non-permissive conditions. In view of the increased resistance of $\chi$1776 and $\chi$1876 to infection by PlL4, it was decided to study the production of other phages in $\chi$1776 under non-permissive conditions. One reason for doing this is that the changes in $\chi$1776's cell surface that result in resistance to well-studied E. coli phages can also result in sensitivity to other phages which have not been well studied and which therefore might be capable of transduction. Evidence for the reversal of phage sensitivity patterns during the derivation of $\chi$1776 was found. In one experiment, the ability of $\chi$1776 after 0 and 4 hours starvation in BSG and ML+glucose to be productively infected with T6 phage was measured. T6 can be produced inefficiently by $\chi$1776 under starvation conditions even in the absence of a carbon source. Starvation for 4 hours prior to infection gave better yields than did starvation for 0 hours and this is most likely due to the starvation-induced turnover of proteins and other cellular constituents to provide raw materials for phage development. Latent periods under these conditions were long (2 to 3 hours) and burst sizes small (about 50), however.

Potential for transformation under non-permissive conditions. The fact that $\chi$1776 and $\chi$1876 lyse under growth conditions in the absence of DAP leads to the question as to whether the DNA released by such lysing cells might not be taken up and transform other bacterial cells in the same environment. DNA released by $\chi$1776 and $\chi$1876 during DAP-less death is rapidly degraded when the lysis occurs in cultures of reasonably high density ($10^7$ to $10^9$ cells/ml) in which case the released nucleases are probably present in high enough concentrations to degrade the released DNA. However, such cell densities are not likely during lysis of escaped bacteria in nature and one must therefore determine whether nucleases are present in these natural environments. It was found that DNA is very rapidly degraded when added to the intestinal contents of both conventional and germ-free sacrificed rats and is therefore unlikely to survive long enough to transform other bacteria.

Most microbial geneticists think of the need for incubating gram-negative bacteria at 0° C. in the presence of $CaCl_2$ followed by a rapid temperature shift to 30° to 42° C. to obtain transformation, and although these conditions are not likely to be encountered in nature, such conditions might not be necessary. For example, it might be possible to obtain transformation of E. coli with plasmid DNA at 37° C. by simultaneous infection with a helper virus, although such a possibility has never been examined.

FEATURES AFFECTING UTILITY OF STRAINS

Transformability. $\chi$1776 is more transformable with pSC101 plasmid DNA than its ancestor $\chi$1841 ($\chi$1488 Nal$^r$) but less transformable than its ancestor $\chi$1849. These results indicate that the $\Delta$[gal-uvrB] mutation improves transformability and that the mutations conferring bile salts sensitivity decrease it. Several different transformation procedures were tried and since none of the previously described methods were satisfactory for $\chi 1776$ a new procedure was developed as described hereinafter.

Plasmid curing. The growth of $\chi 1876$ at 41° C. but not at 37° C. results in loss of the pSC101 plasmid. This feature might be of some use. Derivatives of $\chi 1876$ cured of pSC101 were also examined to see if they gave higher yields of pSC101 transformants than $\chi 1776$ and no difference was measurable.

Minicell production. During the construction of $\chi 1776$, an effort was made to always select good minicell producers. $\chi 1776$ and $\chi 1876$ cultures possess 1 to 2 minicells per cell. These have been easily purified from the parental cells that produce them by two successive bandings on linear 5 to 20% sucrose in BSG gradients using the SW 27 rotor in a Beckman preparative ultracentrifuge to yield minicell preparations that contain only 1 contaminating bacterial cell in $10^6$ to $10^7$ minicells. It should be mentioned that these surviving contaminating cells can be completely eliminated by incubating the minicells in a growth medium lacking DAP. Since minicells can neither grow nor divide, they are completely resistant to DAP starvation and minicells from $\chi 1876$ retain the pSC101 plasmid in an undergraded state during 24 hours of starvation for DAP and thymine.

Since the minicells produced by $\chi 1776$ and $\chi 1876$ can survive for long periods of time, some comments are in order about their potential for transmission of genetic information. About 1 out of 10,000 plasmid-containing minicells can be productively infected with T4 bacteriophage and yield a small burst after a prolonged latent period. P1kc can also infect minicells harboring the ColVB-trp plasmid ($110 \times 10^6$ daltons) and can yield transducing phages capable of giving Trp+ transductants. In these experiments, 1 out of 10,000 minicells was productively infected, the burst size was 10 and about 1 out of 500 P1kc particles was capable of transduction of a trp$^-$ strain. Thus, the overall yield of transducing phages was extremely low.

In terms of conjugational transmission of plasmid DNA from minicells, it is known that minicells can act as recipients for plasmid DNA. When these minicell recipients come from an F$^-$ strain and are therefore DNA deficient, they cannot convert conjugationally transferred single-stranded plasmid DNA to a double-stranded circular form and cannot carry out transcription and translation that would be necessary to express the donor phenotype. Minicells produced by a strain harboring a conjugative plasmid can, however, transfer that plasmid at low frequency to F$^-$ cells. Since plasmid-containing minicells can carry out transcription and translation, it is remotely possible that minicells harboring a non-conjugative plasmid might be able to receive conjugative plasmid single-stranded DNA and then convert this to a double-stranded circular form and carry out the synthetic activities to permit the minicell to become a conjugationally proficient donor.

Monitoring and precluding contamination during recombinant DNA molecule experiments. $\chi 1776$ and $\chi 1876$ are resistant to nalidixic acid, cycloserine and trimethoprim and since resistance to nalidixic acid and cycloserine among bacteria in nature is rare and is not known to be plasmid mediated, these antibiotics are useful additives to cultures of $\chi 1776$ and derivatives as a means to preclude contamination of cultures with robust microorganisms from the laboratory environment. This may be particularly important as a means to preclude transformation of a robust contaminant during DNA cloning experiments. In this regard, it should be mentioned that nalidixic acid is stable to autoclaving at normal pH's and thus is difficult to destroy before disposal into the environment. Cycloserine may be preferable since it is less expensive and has a normal half life of about one day at 37° C. at neutral pH. It must therefore be prepared freshly each day and suspended in a pH 8 phosphate buffer until use.

In terms of monitoring $\chi 1776$ and $\chi 1876$ in the presence of high concentrations of other microorganisms, the use of nalidixic acid is far superior to use of cycloserine. Nalidixic acid resistance is an infrequent mutational event and nalidixic acid completely obliterates background growth of sensitive cells even when plating $10^9$ cells per plate. Cycloserine, on the other hand, permits background growth of sensitive cells when plating densities exceed $10^7$ cells per plate.

The testing data obtained indicate that $\chi 1776$ possesses properties in conformance with the stated goals for genetically constructing a safer, more useful host microorganism for recombinant DNA molecule research. Improvements can be made, however; these improvements are as follows:

i. thyA mutation reverts at low frequency—replace with non-reverting ΔthyA57 mutation.
ii. thymineless death leads to accumulation of deoB and deoC mutants that are efficient scavengers of thymine—introduce deoA and upp mutations to abolish ability to use thymine.
iii. DNA degradation during thymineless death is not as rapid or complete as would be desirable—introduce deoA and upp mutations and polA(CS) and recA mutations.
iv. mutations conferring sensitivity to bile, ionic detergents, drugs, antibiotics, etc. and Con$^-$ phenotype revert at low frequency—add additional mutations in con, rfa, lpcA and/or lpcB genes.
v. Δ29[bioH-asd] mutation confers resistance to λ thus precluding use of λ cloning vectors—replace with dapA or dapE mutation.
vi. transformability can be improved—introduce endA mutation.

All of the above-mentioned improvements have been shown to work and methods have been developed and implemented in the genetic construction of other safer, more useful hosts for recombinant DNA molecule research (see Charts D and E).

TABLE 3

| Number | Plasmid | Incompatibility Group | Plasmid Genotype and Phenotype |
|---|---|---|---|
| $\chi 1632^a$ | pSC101 | — | Tc$^r$ |
| $\chi 1779$ | F' | IncFI | his$^+$ |
| $\chi 1780$ | R64drd11 | IncIα | drd11 Sm$^r$ Tc$^r$ |
| $\chi 1782$ | R6K | IncX | Sm$^r$ Ap$^r$ |
| $\chi 1783$ | R549drd1 | IncIα | drd1 Sm$^r$ Km$^r$ |
| $\chi 1784$ | R100drd1 | IncFII | drd1 Tc$^r$ Cm$^r$ Su$^r$ Sm$^r$ Sp$^r$ |

TABLE 3-continued

| Number | Plasmid | Incompatibility Group | Plasmid Genotype and Phenotype |
|---|---|---|---|
| χ1785 | R16 | IncO | $Sm^r\ Su^r\ Tc^r$ |
| χ1786 | RP4 | IncPI | $Ap^r\ Tc^r\ Km^r$ |
| χ1787 | N-3 | IncN | $Tc^r\ Sm^r\ Su^r$ |
| χ1788 | R40a | IncC | $Ap^r\ Km^r\ Su^r$ |
| χ1789 | R27 | IncH | $Tc^r$ |
| χ1791 | R349 | IncT | $Ap^r\ Km^r$ |
| χ1792 | R1drd19 | IncFII | $drd19\ Cm^r\ Km^r\ Ap^r\ Sm^r\ Sp^r\ Su^r$ |
| χ1793 | S-a | IncW | $Sm^r\ Cm^r\ Su^r\ Km^r$ |
| χ1895 | R391 | IncJ | $Km^r$ |
| χ1896 | R471a | IncL | $Ap^r$ |
| χ1898 | R69/2 | IncM | $Ap^r\ Km^r$ |
| χ1900 | R72 | Inc10 | $Km^r$ |
| χ1901 | R71a | Inc9 | $Ap^r\ Sm^r\ Cm^r\ Tc^r\ Su^r$ |
| χ1906 | R648 | IncIα | $Ap^r\ Sm^r\ Km^r$ |
| χ1907 | R66a-1 | IncIα | $Ap^r\ Sm^r\ Km^r$ |
| χ1924 | pR0164 | IncPI | $Tp^r\ Cb^r$ |
| χ2026 | R15 | IncN | $Sm^r\ Su^r$ |
| χ2027 | R831 | IncL | $Sm^r\ Km^r$ |

[a]All plasmids in χ1753 background except χ1632 which has the chromosomal genotype: thr-1 leu-6 tonA21 lacY1 supE44 λ⁻ thi-1.

TABLE 4

Phenotypic Properties of χ1776

| Phenotype | Responsible Mutation(s) |
|---|---|
| Requires DAP | dapD8 Δ29[bioH-asd] |
| Requires threonine | Δ29[bioH-asd] |
| Requires methionine | metC65 Δ29[bioH-asd] |
| Requires biotin | Δ40[gal1-uvrB] Δ29[bioH-asd] |
| Requires thymidine | thyA57* |
| Cannot use galactose for growth | Δ40[gal1-uvrB] |
| Cannot use maltose for growth | Δ29[bioH-asd] |
| Cannot use glycerol for growth | Δ29[bioH-asd] |
| Cannot synthesize colanic acid | Δ40[gal1-uvrB] |
| Sensitive to UV (defective in dark and photo repair) | Δ40[gal1-uvrB] |
| Sensitive to glycerol (aerobic) | Δ29[bioH-asd] |
| Sensitive to bile salts, ionic detergents, antibiotics and drugs | rfb-2 plus additional mutations oms-1 and probably oms-2 |
| Resistant to nalidixic acid | nalA25 |
| Resistant to cycloserine | cycA1 cycB2 |
| Resistant to chlorate (anaerobic) | Δ40[gal1-uvrB] |
| Resistant to trimethoprim | thyA57* |
| Resistant to T1, T5, φ80 | tonA53 |
| Resistant to λ and 21 | Δ29[bioH-asd] |
| Partially resistant to P1 | rfb-2 plus additional mutations oms-1 and probably oms-2 |
| Conjugation defective | Δ40[gal1-uvrB] rfb-2 plus additional mutations oms-1 and probably oms-2 |
| Produces minicells | minA1 minB2 |
| Temperature sensitive | oms-2 mutation linked to thyA57* |
| at 42° C. | plus oms-1 in conjunction with rfb-2 |

The thyA57* mutation may be derived from the ΔthyA57 allele but since it reverts it has been designated with an asterisk.

TABLE 5

Stability of Genetic Markers in χ1776 and χ1876[a]

| Reversion to | Revertant Frequency in χ1776 | Revertant Frequency in χ1876 |
|---|---|---|
| Dap⁺ | $<2.6 \times 10^{-10}$ | $<1.7 \times 10^{-9}$ |
| Bio⁺ | $<2.6 \times 10^{-10}$ | $<1.7 \times 10^{-9}$ |
| Mal⁺ | $<2.6 \times 10^{-10}$ | $<1.7 \times 10^{-9}$ |
| Gal⁺ | $<2.6 \times 10^{-10}$ | $<1.7 \times 10^{-9}$ |
| Met⁺ | $<2.6 \times 10^{-10}$ | $<1.7 \times 10^{-9}$ |
| Thr⁺ | $<2.6 \times 10^{-10}$ | $<1.7 \times 10^{-9}$ |
| Thy⁺ (CAA)[b] | $1.8 \times 10^{-9d}$ | $1.5 \times 10^{-8d}$ |
| Thy⁺ (SMA)[c] | $9.8 \times 10^{-9d}$ | $6.7 \times 10^{-9d}$ |

[a]Cultures of χ1776 and χ1876 were grown with shaking for 12 hr at 37° C. The cultures were sedimented, washed once with BSG + DAP, and the pellet was suspended at one-fortieth of the original volume in BSG + DAP + nalidixic acid (25 μg/ml). A minimum of 0.8 ml of the undiluted χ1776 and 0.2 ml of the undiluted χ1876 cultures were spread on each type of medium selecting for revertants; 0.4 ml, 0.1 ml and 0.1 ml of the $10^{-1}$, $10^{-2}$, and $10^{-3}$ dilutions, respectively, were also plated.
[b]These Thy⁺ revertants were isolated on MA + 1% Casamino acids, 0.5% Glc, DAP, Bio.
[c]These Thy⁺ revertants were isolated on MA + 0.5% Glc, Thr, Met, DAP, Bio (Supplemented Minimal Agar).
[d]The apparent frequencies of Thy⁺ revertants were slightly higher than indicated since some Thy⁻ deoB or deoC mutants were able to form colonies on these plates (presumably due to release of thymine as a consequence of thymineless death of the majority of cells). The mean frequency of such deoB or deoC mutants was $1.3 \times 10^{-9}$.

TABLE 6

Stability of Phenotypic Traits in χ1776 and χ1876[a]

| Strain | Medium for selection | Phenotypic traits | Frequency | Derived Strains |
|---|---|---|---|---|
| χ1776 | MA + CAA, DAP, Bio, Glc + 2 μg thymine/ml | Require low levels of thymine | $1.1 \times 10^{-6}$ | — |
|  |  | Resistant to Thd and dAdo (deoB)[b] | $1.0 \times 10^{-6}$ | χ1931 |
|  |  | Sensitive to Thd and dAdo (deoC)[b] | $1.3 \times 10^{-7}$ | χ1930 |
| χ1776 | L agar + DAP, Thd at 42° C. | See text | $1.7 \times 10^{-5c}$ | χ1929 |
| χ1876 | MacConkey agar + DAP, Thd, Bio | Large colony types that plate at high efficiency on MacConkey Agar and L agar + 0.15% bile salts | $2.5 \times 10^{-9}$ | — |
|  |  | Small colony types that plate at high plating efficiency on MacConkey agar but do not plate on L agar + 0.15% bile salts | $6.3 \times 10^{-9}$ | — |
| χ1776 | MacConkey agar + DAP, Thd, Bio | Large colony types that plate at | $1.3 \times 10^{-9}$ | χ1925 |

TABLE 6-continued

Stability of Phenotypic Traits in $\chi$1776 and $\chi$1876[a]

| Strain | Medium for selection | Phenotypic traits | Frequency | Derived Strains |
|---|---|---|---|---|
| | | high plating efficiency on MacConkey agar and L agar + 0.15% bile salts | | |
| | | Small colony types that plate at high plating efficiency on MacConkey agar but do not plate on L agar + 0.15% bile salts | $6.0 \times 10^{-8}$ | $\chi$1926 |
| $\chi$1776 | L agar + DAP, Thd + 0.15% bile salts | Small colony types that plate on L agar + 0.15% bile salts but not on MacConkey agar | $7.8 \times 10^{-6}$ | $\chi$1927 |
| $\chi$1776 | Penassay agar + DAP, Thd + 0.75% bile salts | Large colonies that plate on MacConkey agar | $5.0 \times 10^{-10}$ | — |
| $\chi$1776 | Penassay agar + DAP, Thd + 0.37% bile salts | Large colonies that plate on MacConkey agar | $1.0 \times 10^{-9}$ | — |
| $\chi$1776 | Penassay agar + DAP, Thd + 0.1% sodium dodecyl sulfate | — | $1.0 \times 10^{-10}$ | — |
| $\chi$1776 | Penassay agar + DAP, Thd + 0.1% sarkosyl | Large colony type | $5.0 \times 10^{-9}$ | — |
| | | Small colony type | $1.5 \times 10^{-9}$ | — |

[a]Cultures were grown to exponential phase in L broth + DAP, Thd, sedimented by centrifugation, concentrated by suspension in L broth + DAP, Thd and plated on media indicated.
[b]Resistant or sensitive to 1 mM thymidine and 1 mM deoxyadenosine in MA.
[c]Frequency based on titer of regular-sized colonies that would grow at 42° C. after restreaking reasonably dense suspensions on L agar + DAP, Thd. These same suspensions grew better at 37° C. than at 42° C., however. There were twice the frequency of small colonies that did not grow at 42° C. when restreaked.

TABLE 7

Selection of Various Transductant Types from $\chi$1776[a]

| Marker Selected | Plating Medium | No. Revertants per ml | No. Transductants per ml | Transductant Frequency |
|---|---|---|---|---|
| Thr+ | MA+Met,Bio,DAP,Thd,Glu | 0 | 65 | $2.3 \times 10^{-7}$ |
| Mal+ | MA+Thr,Met,Bio,DAP,Thd,Mal | 0 | 32 | $1.1 \times 10^{-7}$ |
| Thr+Mal+ | MA+Met,Bio,DAP,Thd,Mal | 0 | 42 | $1.5 \times 10^{-7}$ |
| Glyc+ | MA+Thr,Met,Bio,DAP,Thd,Glyc | 0 | 28 | $9.8 \times 10^{-8}$ |
| Bio+ | MA+Thr,Met,DAP,Thd,Glu | 500[b] | 243[b] | $8.6 \times 10^{-7}$ |
| Bio+ | MA+CAA,DAP,Thd,Glu | 0 | 0 | $<1.7 \times 10^{-8}$ |
| Met+ | MA+Thr,Bio,DAP,Thd,Glu | 0 | 0 | $<1.7 \times 10^{-8}$ |
| Thy+ | MA+Thr,Met,Bio,DAP,Glu | 0 | 180 | $6.3 \times 10^{-7}$ |
| Dap+ | Penassay agar + Thd | 0 | 13 | $4.6 \times 10^{-8}$ |
| Gal+ | MA+Thr,Met,Bio,DAP,Thd,Gal | 0 | 5 | $1.8 \times 10^{-8}$ |

[a]$\chi$1776 was grown in LB containing DAP,Bio,Thd and $2.5 \times 10^{-3}$ M CaCl$_2$ to log phase and P1L4 ($\chi$289) was added at a multiplicity of 0.76. After 30 min at 37° C., Na citrate was added to 0.14 M and after 10 min samples were plated on the indicated media.
[b]When these colonies were picked into drops of BSG + DAP and restreaked on selective media, they failed to give rise to any Bio+ colonies even after one week of incubation.

TABLE 8

Efficiencies of Plating of $\chi$1776 on Various Antibiotic-containing Media[a]

| | MA + 0.5% Glc, 1% CAA, DAP, Bio Thy | | | | | L agar DAP, Thy | | | | | EMB + 1% Mtl, Ade, DAP, Bio, Thy, Pdx | | | | |
|---|---|---|---|---|---|---|---|---|---|---|---|---|---|---|---|
| μg Nal/ml | 0 | 25 | 50 | 75 | 100 | 0 | 25 | 50 | 75 | 100 | 0 | 25 | 50 | 75 | 100 |
| | 1.25 | 1.20 | 1.10 | 0.99 | 1.10 | 1.00 | 1.01 | 0.84 | 0.77 | 0.50 | 0.90 | 0.79 | 0.68 | 0.71 | 0.64 |
| | MA + 0.5% Glc, Thr, Met, DAP Bio, Thy | | | | | L agar + DAP, Thy, Cyc[6b] | | | | | EMB + 1% Mtl, Ade, DAP, Bio, Thy, Pdx Cyc[6b] | | | | |
| μg Nal/ml | 0 | 25 | 50 | 75 | 100 | 0 | 25 | 50 | | | 0 | 25 | 50 | 75 | 100 |
| | 1.33 | 1.30 | 1.30 | 1.30 | 1.00 | 1.00 | 0.98 | 0.79 | | | 1.02 | 0.90 | 0.99 | 0.88 | 0.90 |
| | MA + 0.5% Glc, Thr, Met, DAP Bio, Thy | | | | | | | | | | | | | | |
| μg Cyc/ml | 1.5 | 5 | 10 | 15 | 20 | 25 | | | | | | | | | |
| | 0.70 | 1.10 | 0.95 | 1.30 | 0.91 | 1.10 | | | | | | | | | |

[a]Strains were grown exponentially in L broth + Thy + DAP at 37° C. to a density of approximately $1 \times 10^8$ cells/ml. Each culture was diluted in BSG + DAP + Thy and plated on the media listed in the table. The cell titer determined on L agar + DAP + Thy was arbitrarily designated as a plating efficiency of 1.00 and was used as the standard for determining all other efficiencies of plating.
[b]Cyc: cycloserine; the superscript indicates the final concentration (μg/ml) in the medium.

TABLE 9

Cross-streak Tests for Phage Sensitivity[a]

| | Bacterial strain[b] | | | | | | Bacterial strain[b] | | | | |
|---|---|---|---|---|---|---|---|---|---|---|---|
| Phage | $\chi$1833 | $\chi$1841 | $\chi$1849 | $\chi$1776 | $\chi$1925 | Phage | $\chi$1833 | $\chi$1841 | $\chi$1849 | $\chi$1776 | $\chi$1925 |
| T1 | S | S | R | R | R | φII | R | S | S | S | S |
| T2 | S | S | S | S | S | φW | R | R | S | R | S |

TABLE 9-continued

Cross-streak Tests for Phage Sensitivity[a]

| Phage | Bacterial strain[b] ||||| Phage | Bacterial strain[b] |||||
|---|---|---|---|---|---|---|---|---|---|---|---|
| | χ1833 | χ1841 | χ1849 | χ1776 | χ1925 | | χ1833 | χ1841 | χ1849 | χ1776 | χ1925 |
| T3 | R | R | S | S | S | φH | S | S | S | S | S |
| T4 | S | S | S | S | S | PV | S | S | S | R | S |
| T5 | S | S | R | R | R | Qβ | R | R | R | R | R |
| T6 | S | S | S | S | S | MS-2 | R | R | R | R | R |
| T7 | S | S | S | S | S | R17 | R | R | R | R | R |
| λvir | S | S | R | R | R | fcanl | R | R | R | R | R |
| 434 | S | S | S | S | S | f1 | R | R | R | R | R |
| φ80 | S | R | R | R | R | If2 | R | R | R | R | R |
| P1L4 | S | S | S | R | S | 6SR | S | S | S | S | S |
| D108 | S | S | S | R | S | Ffm | R | R | R | R | R |
| Mu-1 | S | S | R | R | R | Br60 | S | S | S | R | S |
| φ12 | ND | S | R | S | R | FP1 | S | R | S | R | R |
| φ14 | S | R | S | S | S | FP3 | S | S | S | S | S |
| φ15 | ND | R | S | S | S | BR10 | S | S | S | S | S |
| 21 | ND | S | ND | R | ND | BF23 | S | S | S | S | S |
| S13 | R | R | S | S | S | C21 | R | R | S | R | S |

[a]Phage sensitivity was determined by cross-straking full loopfuls of log-phase bacterial cultures against phage on EMB + 0.1% glucose, DAP, Thy (Curtiss, 1965). χ1766 and χ1876 form light red streaks on EMB + 0.1% glucose due to what appears to be periplasmic leaking; it was therefore necessary to score these streaks on the basis of detectable lysis or no lysis after 12 and/or 24 hr incubation at 37° C.

[b]Identical results were obtained for both χ1776 and χ1876 and likewise for χ1925 and χ1928. Two other bile salts resistant revertants of χ1776, χ1926 and χ1927 (see Table 6), retained the phage sensitivity pattern of χ1776 for response to D108 and φ12 but became sensitive to P1L4. They were not tested for response to φW, PV, Br60 and C21 which also distinguish χ1776 from χ1925. ND = not done.

TABLE 10

Ability of P1L4 to Form Plaques and Transduce χ1776 and its Ancestors

| Host Strain | Efficiency of plating[a] | Transduction[b] ||
|---|---|---|---|
| | | Marker Selected | Frequency |
| χ1488 | 0.65 | — | — |
| χ1678 | 0.80 | — | — |
| χ1697 | 0.87 | — | — |
| χ1702 | 1.64 | Ilv+ | 3.9 × 10⁻⁵ |
| χ1777 | 1.47 | — | — |
| χ1820 | 0.96 | Ilv+ | 5.2 × 10⁻⁵ |
| χ1845 | 1.47 | Ilv+ | 1.0 × 10⁻⁵ |
| χ1846 | 1.12 | — | — |
| χ1849 | 0.93 | Ilv+ | 1.5 × 10⁻⁵ |
| χ1855 | <1.3 × 10⁻⁴ | — | — |
| χ1859 | <1.3 × 10⁻⁴ | Ilv+ | 7.6 × 10⁻⁶ |
| χ1864 | <1.3 × 10⁻⁴ | Thr+ | 1.5 × 10⁻⁶ |
| | | Thr+ | 3.0 × 10⁻⁶ |
| χ1776 | <1.3 × 10⁻¹⁰ | Thr+ | 2.3 × 10⁻⁷ |

[a]P1L4 (χ289) was used and all strains were grown in L broth + DAP, Thd + 2.5 × 10⁻³ M CaCl₂, to log phase. Preadsorption was permitted for 30 min at 37° C. prior to plating on L agar by the soft agar method. 2.5 × 10⁻³ M CaCl₂, DAP and Thd were added to L agar and L soft agar. Plating on χ289 gave 7.5 × 10¹⁰ pfu/ml; this was taken as an efficiency of plating of 1.0.

[b]Representative data from transductions with P1L4 (χ289) and P1L4 grown on other χ289 derivatives. P1L4 was added at a multiplicity of about one and preadsorption occurred during a 30 min incubation at 37° C. prior to addition of citrate and direct plating on selective MA.

TABLE 11

Minimal Inhibitory Concentrations for Various Antibiotics, Mutagens, Drugs, Detergents and Bile Salts[a]

| Strain | Number of Cells Spotted | MIC (μg/ml) |||||||||
|---|---|---|---|---|---|---|---|---|---|---|
| | | Ap | Cm | Fos | Km | Nal | Rif | Cyc | Sm | Sp | Tc |
| χ289 | 1.8 × 10⁶ | 3.1 | 12.5 | 200 | 25 | 6.25 | 25 | 6.25 | 50 | 100 | 6.25 |
| | 1.8 × 10⁴ | 3.1 | 6.25 | 100 | 6.25 | 3.1 | 25 | 3.1 | 50 | 100 | 3.1 |
| | 1.4 × 10² | 3.1 | 6.25 | 50 | 3.1 | 1.6 | 6.25 | 1.6 | 25 | 100 | 1.6 |
| χ1841 | 1.9 × 10⁶ | 12.5 | 12.5 | 800 | 25 | >400 | 25 | 50 | >400 | 100 | 6.25 |
| | 1.6 × 10⁴ | 3.1 | 6.25 | 800 | 12.5 | >400 | 12.5 | 25 | >400 | 100 | 3.1 |
| | 1.2 × 10⁻² | 3.1 | 6.25 | 400 | 12.5 | >400 | 12.5 | 25 | >400 | 50 | 1.6 |
| χ1776 | 1.0 × 10⁶ | 3.1 | 3.1 | 100 | 3.1 | 400 | 0.8 | 50 | 25 | 50 | 3.1 |
| | 4.9 × 10³ | 3.1 | 1.6 | 100 | 3.1 | 200 | 0.4 | 25 | 12.5 | 50 | 1.6 |
| | 5.5 × 10¹ | 3.1 | 0.8 | 50 | 3.1 | 200 | 0.1 | 25 | 6.25 | 25 | 0.8 |
| χ1925 | 1.0 × 10⁶ | 3.1 | 3.1 | 100 | 6.25 | >400 | 6.25 | 50 | 50 | 100 | 3.1 |
| | 1.0 × 10⁴ | 3.1 | 1.6 | 50 | 6.25 | >400 | 3.1 | 25 | 50 | 50 | 1.6 |
| χ1876 | 1.3 × 10⁻⁶ | 3.1 | 3.1 | 100 | 3.1 | 400 | 0.8 | 50 | 50 | 50 | 100 |
| | 4.0 × 10³ | 3.1 | 0.8 | 100 | 3.1 | 200 | 0.4 | 25 | 25 | 50 | 50 |
| | 4.3 × 10¹ | 3.1 | 0.8 | 50 | 3.1 | 200 | 0.1 | 25 | 6.25 | 25 | 50 |

| Strain | Number of Cells Spotted | MIC (μg/ml) ||||||| Brij 58 | Bile Salts |
|---|---|---|---|---|---|---|---|---|---|---|
| | | Tp | AO | EB | MC | MMS | SDS | SL | DC | | |
| χ289 | 1.8 × 10⁶ | 6.25 | >100 | >100 | 25 | ND | 12800 | 12800 | 12800 | 12800 | 6000 |
| | 1.8 × 10⁴ | 6.25 | >100 | >100 | 6.25 | ND | 12800 | 12800 | 12800 | 12800 | 6000 |
| | 1.4 × 10² | 3.1 | >100 | >100 | 6.25 | ND | 12800 | 12800 | 12800 | 12800 | 6000 |
| χ1841 | 1.9 × 10⁶ | 6.25 | >100 | >100 | 25 | 1600 | 12800 | 12800 | 12800 | 12800 | 6000 |
| | 1.6 × 10⁴ | 6.25 | >100 | >100 | 12.5 | 1600 | 12800 | 12800 | 12800 | 12800 | 6000 |
| | 1.2 × 10² | 1.6 | >100 | >100 | 12.5 | 800 | 12800 | 12800 | 12800 | 12800 | 6000 |
| χ1776 | 1.0 × 10⁶ | 200 | >100 | >100 | 6.25 | 1600 | 400 | 100 | 800 | 12800 | 750 |

TABLE 11-continued

Minimal Inhibitory Concentrations for Various Antibiotics,
Mutagens, Drugs, Detergents and Bile Salts[a]

|       |                   |     |      |      |      |      |       |       |       |       |       |
|-------|-------------------|-----|------|------|------|------|-------|-------|-------|-------|-------|
|       | $4.9 \times 10^3$ | 200 | >100 | >100 | 0.4  | 1600 | 200   | 100   | 400   | 12800 | 370   |
|       | $5.5 \times 10^1$ | 100 | >100 | >100 | 0.2  | 400  | 200   | 50    | 200   | 12800 | 190   |
| χ1925 | $1.0 \times 10^6$ | ND  | >100 | >100 | 6.25 | ND   | 12800 | 12800 | 12800 | 12800 | 12800 |
|       | $1.0 \times 10^4$ | ND  | >100 | >100 | 0.4  | ND   | 12800 | 12800 | 12800 | 12800 | 6000  |
| χ1876 | $1.3 \times 10^6$ | 200 | >100 | >100 | 6.25 | 1600 | 400   | 100   | 800   | 12800 | 750   |
|       | $4.0 \times 10^3$ | 200 | >100 | >100 | 0.8  | 1600 | 200   | 100   | 400   | 12800 | 370   |
|       | $4.3 \times 10^1$ | 200 | >100 | >100 | 0.2  | 400  | 200   | 50    | 200   | 12800 | 190   |

[a]Each culture was grown to a titer of ca. $1 \times 10^8$ cells/ml in L broth + DAP + Thy; the culture was then diluted and 0.005 ml samples of the $10^\circ$, $10^{-2}$ and $10^{-4}$ dilutions were spotted on Penassay agar + DAP + Thy + test compound. Growth or inability to grow was determined after 24 hours of incubation at 37° C.
The minimal inhibitory concentration (MIC) represents the least amount of test compound necessary to allow no growth or less than 3 small colonies/plate.
All drug concentrations are in μg/ml.
ND indicates not determined.
Abbreviations for test compounds: Ap: ampicillin; Cm: chloroamphenicol; Fos: fosfoymcin; Km: kanamycin; Nal: nalidixic acid; Rif: rifampin; Cyc: cycloserine; Sm: streptomycin; Sp: spectinomycin; Tc: tetracycline; Tp: trimethoprim; AO: acridine orange; EB: ethidium bromide; MC: mitomycin C; MMS: methyl methane sulfonate; SDS: sodium dodecyl sulfate; SL: sarkosyl; DC: deoxycholate.

TABLE 12

Survival of Bacteria During Passage Through the Intestinal Tract of Rats[a]

| Strain | Total bacteria fed/rat | Number of rats/strain | Mean titer/rat/0.1 g of feces at designated hours after feeding | | | | | | | |
|---|---|---|---|---|---|---|---|---|---|---|
| | | | 0 | 6 | 12 | 18[b] | 24 | 48 | 72 | 120 |
| χ1833 | $1 \times 10^{10}$ | 6 | <4 | $9 \times 10^7$ | $4 \times 10^7$ | $8 \times 10^5$ | $4 \times 10^6$ | $1 \times 10^5$ | $2 \times 10^3$ | >4 |
| χ1922 | $4 \times 10^9$ | 3 | <4 | $2 \times 10^7$ | $2 \times 10^6$ | $8 \times 10^3$ | $6 \times 10^4$ | $2 \times 10^2$ | <4 | — |
| χ1841 | $3 \times 10^{10}$ | 9 | <4 | $1 \times 10^2$ | $3 \times 10^6$ | $2 \times 10^4$ | $1 \times 10^5$ | $4 \times 10^2$ | <4 | — |
| χ1846 | $5 \times 10^{10}$ | 3 | <4 | $4 \times 10^7$ | $4 \times 10^5$ | $4 \times 10^4$ | $8 \times 10^4$ | <4 | — | — |
| χ1849 | $9 \times 10^8$ | 3 | <4 | $1 \times 10^5$ | $6 \times 10^3$ | $2 \times 10^2$ | <4 | <4 | — | — |
| χ1864 | $5 \times 10^9$ | 3 | <4 | <4 | <4 | <4 | <4 | <4 | — | — |
| χ1776 | $4 \times 10^9$ | 9 | <4 | <4 | <4 | <4 | <4 | <4 | — | — |
| χ1776-9[c] | $3 \times 10^9$ | 3 | <4 | <4 | <4 | — | <4 | <4 | — | — |
| χ1776-14[c] | $1 \times 10^{10}$ | 3 | <4 | <4 | <4 | — | <4 | <4 | — | — |
| χ1776-18[c] | $3 \times 10^8$ | 3 | <4 | <4 | <4 | — | <4 | <4 | — | — |
| χ1776-23[c] | $1 \times 10^{10}$ | 3 | <4 | <4 | <4 | — | <4 | <4 | — | — |
| χ1776-32[c] | $8 \times 10^9$ | 3 | <4 | <4 | <4 | — | <4 | <4 | — | — |
| χ1929[d] | $1 \times 10^9$ | 3 | <4 | <4 | <4 | — | <4 | <4 | — | — |
| χ1930[d] | $4 \times 10^9$ | 3 | <4 | <4 | <4 | <4 | <4 | <4 | — | — |
| χ1925[d] | $6 \times 10^9$ | 3 | <4 | $5 \times 10^3$ | $3 \times 10^3$ | — | <4 | <4 | — | — |
| χ1926[d,e] | $6 \times 10^9$ | 3 | <4 | <4 | <4 | — | <4 | <4 | — | — |
| χ1876 | $7 \times 10^9$ | 9 | <4 | <4 | <4 | <4 | <4 | <4 | — | — |
| χ1928[d,e] | $1 \times 10^{10}$ | 3 | <4 | <4 | $2 \times 10^4$ | — | <4 | <4 | — | — |
| χ1876+Tc[e,f] | $1 \times 10^{10}$ | 3 | <4 | <4 | $8 \times 10^5$ | — | $3 \times 10^2$ | <4 | — | — |
| χ1928+Tc[e,f] | $1 \times 10^{10}$ | 3 | <4 | <4 | $5 \times 10^7$ | — | $5 \times 10^4$ | <4 | — | — |

[a]Overnight cultures of the strains were inoculated into an appropriate volume (100 or 500 ml) of L broth + DAP + Thy + Nal (100 μg/ml, 40 μg/ml and 25 μg/ml, respectively) and incubated without aeration in sealed containers at 37° C. Cells were harvested in early stationary phase by centrifugation in a GSA rotor at 7000 rpm for 20 min. The bacteria were suspended in 30 to 40 ml of BSG + DAP + Thy and centrifuged in an SS-34 rotor at 10,000 rpm for 10 min at room temperature. The resulting pellets were suspended in milk + DAP + Thy (Barber's homogenized milk, Birmingham, Ala.) to a final volume of 1.0 ml and titered immediately on L agar + DAP + Thy and on EMB + 1% Mtl + Ade, DAP, Bio, Thy, Pdx (this EMB did not contain yeast extract). Samples of 0.2 to 0.25 ml of the milk suspension containing $3 \times 10^9$ to $5 \times 10^{10}$ cells were orally administered to three weanling rats/ strain (Charles River, Wilmington, Mass. by using a 1.0 ml syringe equipped with a cut-off 24 gauge needle with a soldered ball at the tip to permit easy insertion down the esophagus. All subsequent retests for a given strain used these same rats. All rats were individually housed in suspended cages. Fresh fecal pellets (0.1 to 0.15g/rat) were collected by gently squeezing the rat and suspended in 4 ml L broth + DAP + Thy + Nal (50 μg/ml) at 0, 6, 12, 24 and 24 hr intervals thereafter. Samplings at 18 hr were included in selected experiments. The fecal pellets were gently homogenized and suspended by use of a sterile tissue grinder and diluted in serial four-fold dilutions ($10^0$, ¼, 1/16, 1/64) in L broth +DAP + Thy + Nal (50 μg/ml) and incubated for 48 hr at 37° C. Titers of these serial dilutions were scored on a growth-no growth basis by spotting a loopful of culture on EMB + Mtl agar (plus supplements) and incubating them for 48 hr at 37° C. This method allowed detection of as few as 4 cells/fecal pellet. For higher titers, the original suspension (before incubation) was diluted in 10-fold increments in BSG + DAP + Thy, plated directly onto EMB + Mtl plates (plus supplements) which were incubated at 37° C. for 48 hr. The genotype of the Mtl+ strains that were recovered were checked for their ability to grow on MA + Glc with no supplements; L agar + DAP + Thy; L agar + Thy; MA + CAA + DAP + Bio + Thy (40 μg/ml) + Glc; MA + CAA + DAP + Bio + Thy (2 μg/ml) + Glc; and MA + CAA + DAP + Bio + Glc.
[b]The 18 hr sample represents only 3 rats/strain.
[c]These derivatives were obtained by picking colonies or papillae from various media on which χ1776 had been plat at high density. All isolates had the same genotypic and phenotypic properties as χ1776 except some of them plated at higher efficiency than χ1776 on media such as MA + CAA, DAP, Thd, Bio; MA + CAA, DAP, Thd, Bio, Glyc; Tryptone agar + DAP, Thd, Bio; etc.
[d]See Table 6 for origin of derivative.
[e]χ1926, χ1928, χ1876+Tc, χ1928+Tc were serially diluted in L broth + DAP + Thy + Nal (25 μg/ml) instead of the usual 50 μg nalidixic acid/ml.
[f]The water of these rats was replaced with 3 mg tetracycline/ml 24 hr before administering the respective strains. At the time of feeding the concentration of tetracycline was reduced to 0.5 mg/ml and maintained throughout the experiment.

UTILITY ASSOCIATED WITH MICROORGANISMS GENETICALLY MODIFIED IN ACCORDANCE WITH THIS INVENTION

Isolation of Mutant Derivatives

It is known that dap cells surviving DAP-less death in a minimal medium are enriched with respect to mutants that cannot grow in said medium and therefore do not undergo DAP-less death. It is also known that thyA cells surviving thymineless death in a minimal medium are enriched with respect to mutants that cannot grow in said medium and therefore do not undergo thymineless death. The standard method for mutant enrichment in dap+ thy+ strains utilizes the addition of ampicillin and/or cycloserine to kill non-mutant cells and enrich for mutant cells. The availability of strains such as χ1776, χ1972, χ1976 and χ2076 that require both diaminopimelic acid and thymidine for growth permits the development of a mutant enrichment procedure that utilizes the combined benefits of DAP-less death, thymineless death and ampicillin+cycloserine enrichment for the isolation of rare mutants from these strains. Such a method has been developed and achieves the stated aims. Mutant derivatives of $\chi$1776, $\chi$1972, $\chi$1976 and $\chi$2076 should be very useful for many studies with recombinant DNA molecules and this mutant enrichment technique will therefore have broad utility.

Isolation of Plasmid Vector DNA

Since $\chi$1776, $\chi$1972, $\chi$1976 and $\chi$2076 are very sensitive to ionic detergents, it is essential for success in transforming such strains that any and all DNA preparations used for transformation be free from such ionic detergents. Since these strains are as resistant to non-ionic detergents such as Brij-58, Triton-X100, etc. as are wild-type strains of *E. coli*, it is advisable to use these non-ionic detergents rather than ionic detergents for the isolation of plasmid cloning vector DNA whether containing or not containing foreign DNA for the introduction into these stains by transformation. Methods of cloning vector DNA isolation that do not require use of detergents are even more preferable.

Methods for isolation of plasmid cloning vector DNA have therefore been developed which are based on modifications of the standard methods for preparation of cleared lysates (Guerry et al., 1973) and for ethidium bromide-CsCl centrifugation purification of plasmid DNA (Mukai et al., 1973). These modifications are as follows:

1. When the host strain containing the plasmid cloning vector is a "wild-type-like" host such as W1485, C600, etc., the final concentrations of sodium dodecyl sulfate or sarkosyl used to lyse the lysozyme-generated spheroplasts should be reduced from the usual 1 to 5% to 0.25%. Other methods are as described by Guerry et al. and Mukai et al. except that after removal of ethidium bromide by isopropanol extraction the purified plasmid cloning vector DNA is dialysed at 4° C. against 500 ml of TEN buffer (Tris, 20 mM; EDTA, 2 mM; NaCl, 10 mM; pH 8.0), the buffer being changed every 12 hours over a period of 3 to 4 days to remove all CsCl and residual detergent. This DNA is then stored in TEN buffer at 4° C. and diluted into Tris (0.02M)-NaCl (0.8%) buffer (pH 8.0) for use in transformation. The use of non-ionic detergents for these "wild-type-like" hosts does not give satisfactory yields of plasmid DNA.

2. When the host strain containing the plasmid cloning vector is $\chi$1776 or another similarly modified host, the final concentration of sodium dodecyl sulfate or sarkosyl can be reduced to 0.1% for the lysis of lysozyme-generated spheroplasts. Other procedures are as in 1. above.

3. When the host strain containing the plasmid cloning vector is $\chi$1776 or another similarly modified host, the lysozyme-generated spheroplasts can be lysed by the addition of Brij-58 or another non-ionic detergent to a final concentration of 0.25%. The DNA should be dialysed at 4° C. as described in 1. above but only needs to be dialysed for a period of 24 to 36 hours.

4. When the host strain containing the plasmid cloning vector is $\chi$1776 or another similarly modified host, the lysozyme-generated spheroplasts can be lysed by an osmotic temperature shock by the addition of an equal volume of ice-cold water adjusted to pH 9. Dialysis of DNA can be as in 3. above.

Procedure for Transformation of $\chi$1776

Due to the nature of the cell surface in $\chi$1776 and in other genetically modified microorganisms, existing methods of transformation with plasmid vector DNA give very low yields of transformants. This difficulty can be further intensified depending on the method of plasmid DNA isolation and the extent of dialysis of such DNA as indicated hereinabove. It has therefore been desirable to develop a new procedure for the optimal transformation of $\chi$1776. An enumeration of the steps in the procedure follows:

1. Prepare an overnight culture (18 hours) of $\chi$1776 by growing in 5 ml of L broth+DAP (100 $\mu$g/ml)+Thd (5 $\mu$g/ml) at 37° C. as a standing culture.

2. Dilute the overnight culture 1:10 into 20 ml of L broth+DAP+Thd and incubate at 37° C. with aeration (e.g., shaking) for 3 to 4 hours until the culture reaches an optical density of 0.5 to 0.6 at $A_{600}$.

3. Sediment the cells in the culture by centrifugation at 4° C. for 10 minutes at 8700$\times$g (e.g., at 8500 rpm in SS-34 rotor of Sorvall Refrigerated Centrifuge).

4. Discard the supernatant culture medium and *gently* resuspend the pellet in 10 ml ice-cold 10 mM NaCl.

5. Sediment the cells as in 3 above.

6. Discard the supernatant fluid and *gently* resuspend the pellet in 10 ml ice-cold 75 mM $CaCl_2$ in Tris-HCl (10 mM) buffer (pH 8.4) and place in an ice bucket for 20 to 25 minutes. (Note: The pH of the $CaCl_2$ solution is critical and the pH of $CaCl_2$ solutions has been found to depend on whether anhydrous $CaCl_2$ or $CaCl_2.2H_2O$ is used, the "age" of the opened $CaCl_2$ bottle and the quality of the suspending water. Solutions at pH 8.4 give the optimal yields of transformants.)

7. Sediment the cells as in 3 above.

8. Discard the supernatant fluid and *gently* resuspend the pellet in 2.0 ml of ice-cold 75 mM $CaCl_2$ in Tris-HCl (10 mM) buffer (pH 8.4) and place in ice bucket.

9. Add 100 $\mu$l of plasmid vector and/or recombinant DNA in 0.02M Tris, 0.8% NaCl (pH 8.0) to a clean pyrex test tube in an ice bucket at 0° C. The DNA should be at a concentration of about 0.2 $\mu$g/ml.

10. Then add 200 $\mu$l of chilled cells from 8 above. These should be at a concentration of 0.9 to 2.0$\times 10^9$ colony forming units/ml although lower concentrations of cells (e.g., 2.0$\times 10^8$/ml) give somewhat higher absolute efficiencies of transformation.

11. Keep the tube at ice temperature for 20 to 25 minutes.

12. Then rapidly heat the tube to 42° C. in a water bath and maintain it at that temperature for one minute. Longer incubations at 42° C. have little or no effect in further increasing transformant yield.

13. Then chill the tube in ice bucket for 10 minutes.

14. If the cloning vector is pSC101, pMB9 or a derivative thereof, plate 0.1 ml samples directly on EMB+DAP+Thd+1% Glucose+25 $\mu$g nalidixic acid/ml+12.5 $\mu$g tetracycline/ml. If plating by spreading, distribute the sample over the surface of the plates and allow fluid to dry into the plate. Spreading to dryness reduces transformant yield. The plating medium should be prepared the same day and should not be dried at 42° C. or above since tetracycline is converted to a toxic product.

15. If the cloning vector is pCR1 or a derivative thereof, take 0.1 ml of the transformant mixture and add to 0.9 ml L broth+DAP+Thd+25 $\mu$g nalidixic acid/ml and incubate at 37° C. for 2 hours before plating on EMB+DAP+Thd+1% Glucose+25 μg nalidixic acid/ml+25 μg kanamycin/ml.

16. Incubate the plates for 2 to 3 days at 37° C.

Note: All glassware, centrifuge tubes, etc, should be clean and free from scratches that could accumulate residual detergent used in cleaning.

SPECIFIC USES OF GENETICALLY MODIFIED MICROORGANISMS FOR WORK WITH RECOMBINANT DNA MOLECULES $\chi$1776 (Chart C)—compatible for use with non-conjugative plasmid cloning vectors such as pSC101, pMB9, pCR1, etc.

$\chi$2076 (Chart D)—compatible for use with non-conjugative plasmid cloning vectors such as pSC101, pMB9, pCR1, etc.

$\chi$1963 (Chart E)—compatible for use with $\lambda$-derived cloning vectors that are unable to lysogenize host and are dependent on presence of amber suppressor mutations in host for their replication and maturation with production of infectious phage particles.

$\chi$1961 (Chart E)—Useful for testing $\lambda$ vectors compatible with $\chi$1963 for retention of amber suppressible mutations in vector and compatible for use with $\lambda$ vectors that are unable to lysogenize host and possess amber suppressible mutations that prevent production of phage tails and/or assembly of phage tails to phage heads but which do not prevent phage vector replication or assembly of phage vector heads containing DNA.

$\chi$1972 (Chart E)—Compatible for use with $\lambda$ vectors that can lysogenize host and whose maturation and assembly into infectious phage particles is dependent on presence of amber suppressible mutations in host. Is also compatible for use with non-conjugative plasmid cloning vectors whose maintenance, replication and function is independent of presence of amber suppressor mutations in host.

$\chi$1976 (Chart E)—Compatible for use with non-conjugative plasmid cloning vectors such as pSC101, pMB9, pCR1 and derivatives thereof and with plasmid cloning vectors derived from $\lambda$ such as $\lambda$dv and derivatives thereof.

$\chi$1966, $\chi$1968, $\chi$1969, $\chi$1970, $\chi$1973, $\chi$1974, and $\chi$1975 (Chart E)—These modified hosts are likely to be compatible for use with certain viral and plasmid cloning vectors that have not yet been developed.

A deposit of the *Escherichia coli* K-12 $\chi$1776 has been placed with the American Type Culture Collection, Rockville, Maryland, U.S.A. and has been assigned ATCC No. 31244.

Although emphasis has been placed in this disclosure on the preparation of highly specialized microorganisms derived from *E. coli*, microorganisms in accordance with the practices of this invention are capable of being modified and/or prepared from other bacteria or microorganisms or cells, including eucaryotic microorganisms or cells and procaryotic microorganisms or cells. Yeast molds, algae, Protozoa and other microorganisms or cellular material are capable of modification and/or genetic alteration in accordance with the practices of this invention to be useful as hosts for cloning recombinant DNA molecules and capable of reproduction and/or possessing other useful physical and/or biochemical or genetic properties. Other such microorganisms include the Bacillus bacteria, e.g. *B. subtilis* and variants thereof, *B. licheniformis*, *B. stearothermophilus*, the Pseudomonas, e.g. *P. fluorescens*, *P. putrefaciens*, the Streptomyces, such as *S. aureofaciens*, the Rhizobium, such as species thereof which form root nodules on plants, e.g. legumes, particularly those which fix nitrogen involving a symbiotic relationship between the Rhizobium bacteria and a plant. Other microorganisms usefully altered in accordance with the practices of this invention include the yeasts, such as the Saccharomyces, e.g. *S. cerevisiae*.

In general, as indicated hereinabove, any microorganism or cellular material, particularly a procaryotic microorganism, is capable of alteration in accordance with the practices of this invention to yield a microorganism having the desired characteristics in accordance with this invention.

Following is a listing of the literature or publications cited hereinabove as being of interest in connection with various aspects of the practices of this invention. The disclosures of these publications, more specifically defined in the following listing entitled "Literature Cited", are herein incorporated and made part of this disclosure.

LITERATURE CITED

1. Adams, M. H. 1959. *Bacteriophages*. New York: Interscience Publishers, p. 592.
2. Bachmann, B. J. 1972. Bacteriol. Rev. 36:525–557.
3. Bachmann, B. J., Low, K. B. and Taylor, A. L. 1976. Bacteriol. Rev. 40:116–167.
4. Berg, C. M. and Curtiss, R., III. 1967. Genetics 56:503–525.
5. Bukhari, A. I. and Taylor, A. L. 1971. J. Bacteriol. 105:844–854.
6. Curtiss, R., III. 1964. Genetics 50:679–694.
7. Curtiss, R., III. 1965. J. Bacteriol. 89:28–40.
8. Curtiss, R., III, Charamella, L. J., Stallions, D. R. and Mays, J. A. 1968. Bacteriol. Rev. 32:320–348.
9. Curtiss, R., III, Macrina, F. L. and Falkinham, J. O., III. 1974. *Escherichia coli*—An overview. In: *Handbook Of Genetics*. Vol. I. R. C. King (ed.). pp. 115–133 (New York).
b 10. Demerec, M., Adelberg, E. A., Clark, A. J. and Hartman, P. E. 1966. Genetics 54:61–76.
11. Frazer, A. C. and Curtiss, R., III. 1975. Curr. Topics Microbiol. Immunol. 69:1–84.
12. Gross, J. D. and Caro, L. G. 1966. J. Mol. Biol. 16:269–284.
13. Guerry, P., LeBlanc, D. J. and Falkow, S. 1973. J. Bacteriol. 116:1064–1066.
14. Kellenberger, G., Symonds, N. and Arber, W. 1966. Z. Vererbungsl. 98:247–256.
15. Lennox, E. S. 1955. Virology 1:190–206.
16. Miller, J. H. 1972. *Experiments in Molecular Genetics*. Cold Spring Harbor Laboratory, New York.
17. Mukai, T., Matsubara, K. and Takagi, Y. 1973. Proc. Nat. Acad. Sci. U.S.A. 70:2884–2887.
18. Reiner, A. M. 1969. J. Bacteriol. 97:1431–1436.
19. Stallions, D. R. and Curtiss, R., III. 1971. J. Bacteriol. 105:886–895.
20. Wood, W. B. 1966. J. Mol. Biol. 16:118–133.

Although emphasis in the practices of this invention has been placed on the alteration and/or development of a special microorganism derived from *E. coli*, the practice of this invention in its various embodiments is generally applicable, as indicated hereinabove, to numerous types of microorganisms or cellular material, such as eucaryotic and procaryotic microorganisms, gram-positive and gram-negative microorganisms, yeasts, and other microorganisms. The practices of this invention are also applicable to the alteration, development and/or production of a microorganism useful for the insertion of a recombinant DNA molecule or recombinant DNA therein, the resulting recombinant DNA-containing microorganism or cellular material being capable of growth and replication with the ultimate expression of the characteristics of the recombinant DNA incorporated therein, e.g. in the instance wherein the recombinant DNA controls and/or expresses itself by the production of insulin or a human hormone or other bio-affecting material, there should be produced upon growth or culturing of the recombinant DNA-containing microorganism insulin, human hormone or bio-affecting material.

As will be apparent to those skilled in the art in the light of the foregoing disclosure, many modifications, alterations and substitutions are possible in the practices of this invention without departing from the spirit or scope thereof.

I claim:

1. An *Escherichia coli* microorganism derived from the microorganism $\chi 1276$ selected from the group of derivative microorganisms consisting of $\chi 1488$, $\chi 1678$, $\chi 1679$, $\chi 1702$, $\chi 1777$, $\chi 1820$, $\chi 1845$, $\chi 1846$, $\chi 1849$, $\chi 1855$, $\chi 1859$, $\chi 1864$, and $\chi 1776$.

2. An *Escherichia coli* microorganism derived from the microorganism $\chi 1776$ selected from the group of derivative microorganisms consisting of $\chi 2065$, $\chi 2067$, $\chi 2068$, $\chi 2069$, $\chi 2070$, $\chi 2071$, $\chi 2073$, $\chi 2074$, and $\chi 2076$.

3. An *Escherichia coli* microorganism derived from the microorganism $\chi 1038$ selected from the group of derivative microorganisms consisting of $\chi 1947$, $\chi 1948$, $\chi 1949$, $\chi 1950$, $\chi 1952$, $\chi 1953$, $\chi 1954$, $\chi 1955$, $\chi 1956$, $\chi 1957$, $\chi 1958$, $\chi 1959$, $\chi 1960$, $\chi 1961$, $\chi 1962$, $\chi 1963$, $\chi 1964$, $\chi 1965$, $\chi 1966$, $\chi 1967$, $\chi 1968$, $\chi 1969$, $\chi 1970$, $\chi 1972$, $\chi 1973$, $\chi 1974$, $\chi 1975$ and $\chi 1976$.

4. *Escherichia coli* K-12 $\chi 1776$.
5. *Escherichia coli* K-12 $\chi 1972$.
6. *Escherichia coli* K-12 $\chi 1976$.
7. *Escherichia coli* K-12 $\chi 1961$.
8. *Escherichia coli* K-12 $\chi 1963$.
9. *Escherichia coli* K-12 $\chi 1966$.
10. *Escherichia coli* K-12 $\chi 1968$.
11. *Escherichia coli* K-12 $\chi 1969$.
12. *Escherichia coli* K-12 $\chi 1970$.
13. *Escherichia coli* K-12 $\chi 1973$.
14. *Escherichia coli* K-12 $\chi 1974$.
15. *Escherichia coli* K-12 $\chi 1975$.
16. *Escherichia coli* K-12 $\chi 2076$.
17. *Escherichia coli* K-12 $\chi 1876$.

18. A microorganism in accordance with claim 4 containing recombinant DNA material provided within said microorganism such that said recombinant DNA material becomes part of the genetic structure or makeup of said microorganism.

19. A microorganism in accordance with claim 6 containing recombinant DNA material provided within said microorganism such that said recombinant DNA material becomes part of the genetic structure or makeup of said microorganism.

20. A microorganism in accordance with claim 16 containing recombinant DNA material provided within said microorganism such that said recombinant DNA material becomes part of the genetic structure or makeup of said microorganism.

* * * * *

UNITED STATES PATENT AND TRADEMARK OFFICE
CERTIFICATE OF CORRECTION

PATENT NO. : 4,968,619

DATED : November 6, 1990

INVENTOR(S) : Roy Curtiss, III

It is certified that error appears in the above-identified patent and that said Letters Patent is hereby corrected as shown below:

Column 1, Line 35, "molecule" should read as --molecules--.

Column 1, Line 37, after "microorganisms" insert --such that these recombinant DNA molecules become part of the genetic structure or make-up of the microorganisms--.

Column 3, Line 35, "(C)" should read as --(3)--.

Column 4, Line 58, "$_x$b 1776" should read as --$_x$1776--.

Column 7, Line 6, "partical" should read as --partial--.

Column 10, Line 5, "20761" should read as --2076--.

Column 11, Table 1, Line 16, "tax" should read as --tsx--.

Column 11, Table 1, Line 19, "tax" should read as --tsx--.

Column 12, Table 1, Line 30, "$_x$540" should read as --X540--.

UNITED STATES PATENT AND TRADEMARK OFFICE
CERTIFICATE OF CORRECTION

PATENT NO. : 4,968,619

DATED : November 6, 1990

INVENTOR(S) : Roy Curtiss, III

It is certified that error appears in the above-identified patent and that said Letters Patent is hereby corrected as shown below:

Column 12, Table 1, Line 43, "$Tr^r$" should read as --$T3^r$--.

Column 13, Table 1, Line 13, "laxZ4" should read as --lacZ4--.

Column 13, Table 1, Line 15, "laxZ4" should read as --lacZ4--.

Column 13, Table 1, Line 18, "$Te^r$" should read as --$T3^r$--.

Column 14, Table 1, Line 27, "$t3^r$" should read as --$T3^r$--.

Column 14, Table 1, Line 39, "laxZ" should read as --lacZ--.

Column 15, Table 2, Line 33, "resistace" should read as --resistance--.

Column 15, Table 2, Line 72, "of" should read as --for--.

Column 17, Table 2, Line 17, "uilized" should read as --utilized--.

UNITED STATES PATENT AND TRADEMARK OFFICE
CERTIFICATE OF CORRECTION

PATENT NO. : 4,968,619

DATED : November 6, 1990

INVENTOR(S) : Roy Curtiss, III

It is certified that error appears in the above-identified patent and that said Letters Patent is hereby corrected as shown below:

Column 18, Chart B, Line 68, "$_{102}$ 1276" should read as --$_x$1276--.

Column 23, Chart C, Line 8, "anerobic" should read as --anaerobic--.

Column 23, Chart C, Line 32, "cucA1" should read as --cycA1--.

Column 24, Chart D, Line 65, "F - tonA53 dapD8 minA1 supE42 $\Delta$40[gal-uvrB]$\lambda$-" should read as --F - tonA53 dapD8 minA1 supE42 $\Delta$40[gal-uvrB] --.

Column 26, Chart E, Line 50, "metb1" should read as --metB1--.

Column 26, Chart E, Line 54, "hsd53" should read as --hsdS3--.

Column 26, Chart E, Line 65, "]gal" should read as --[gal--.

Column 31, Line 1, "transuctants" should read as --transductants--.

Column 31, Line 27, "oberved" should read as --observed--.

Column 35, Line 31, "P1L$_4$" should read as --P1L4--.

UNITED STATES PATENT AND TRADEMARK OFFICE
CERTIFICATE OF CORRECTION

PATENT NO. : 4,968,619

DATED : November 6, 1990

INVENTOR(S) : Roy Curtiss, III

It is certified that error appears in the above-identified patent and that said Letters Patent is hereby corrected as shown below:

Column 36, Line 33, "senstivity" should read as --sensitivity--.

Column 37, Line 58, after "for" insert --by--.

Column 60, Line 41, "b 10." should read as --10.--.

Signed and Sealed this

First Day of September, 1992

*Attest:*

DOUGLAS B. COMER

*Attesting Officer*     *Acting Commissioner of Patents and Trademarks*